(12) United States Patent
Okano et al.

(10) Patent No.: US 6,183,970 B1
(45) Date of Patent: Feb. 6, 2001

(54) POLYNUCLEOTIDE PROBE CHIP AND POLYNUCLEOTIDE DETECTION METHOD

(75) Inventors: Kazunori Okano, Shiki; Hideki Kambara, Hachioji; Chihiro Uematsu, Kawasaki; Hiroko Matsunaga, Kokubunji; Takashi Irie, Musashimurayama; Tomoharu Kajiyama, Kokubunji; Kenji Yasuda, Hiki-gun, all of (JP)

(73) Assignee: Hitachi, Ltd., Tokyo (JP)

( * ) Notice: Under 35 U.S.C. 154(b), the term of this patent shall be extended for 0 days.

(21) Appl. No.: 09/383,198

(22) Filed: Aug. 26, 1999

(30) Foreign Application Priority Data

Aug. 27, 1998 (JP) .................................................. 10-241330

(51) Int. Cl.[7] .............................. C12Q 1/68; C07H 21/04
(52) U.S. Cl. ............................................... 435/6; 536/24.3
(58) Field of Search .............................. 435/6; 536/24.3; 935/77

(56) References Cited

U.S. PATENT DOCUMENTS 5,851,772 * 12/1998 Mirzabekov et al. ................... 435/6

OTHER PUBLICATIONS

Igloi, Gabor L., "Variability in the stability of DNA–peptide nucleic acid (PNA) single–base mismatched duplexes: Real–time hybridization during affinity electrophoresis in PNA–containing gels" Proc. Natl. Acad. Sci. USA, Jul. 1998, vol. 95, pp. 8562–8567.*

Vainer et al., "Short tandem repeat typing by capillary array electrophoresis: Comparison of sizing accuracy and precision using different buffer systems," 1997, Genomics, vol. 41, No. 1, pp. 1–9.*
Science, vol. 251, 1991, pp. 767–773.
Proceedings of National Academy of Science USA, vol. 93, 1996,. pp. 4913–4918.
Biophysical Journal, vol. 71, 1996, pp. 1079–1086.
Analytical Biochemisty, vol. 247, 1997, pp. 96–101.

* cited by examiner

*Primary Examiner*—John S. Brusca
*Assistant Examiner*—Young Kim
(74) *Attorney, Agent, or Firm*—Mattingly, Stanger & Malur, P.C.

(57) ABSTRACT

There are beforehand prepared a monomer having a reaction residue and a polynucleotide probe set comprising plural kinds of polynucleotide probes having a residue bonded to the reaction residue. The monomer is mixed with each kind of polynucleotide probes comprising any plural probes selected from the polynucleotide probe set. Each kind of the resultant mixtures is added to each of different small holes to make the mixture into gel matrix. Thus, a polynucleotide probe chip is produced. Sample DNA is forcibly migrated in the gels by electrophoresis. Laser light is projected onto the side face of the chip. The fluorescence emitted from the whole surface of the chip is collectively detected with a high-sensitive two-dimensional detector. Thus, the polynucleotide probe chip, holding various kinds of DNA probes, for detecting DNA can be provided. This chip has high hybridization-efficiency and makes high-sensitivity and high-speed DNA detection possible.

29 Claims, 14 Drawing Sheets

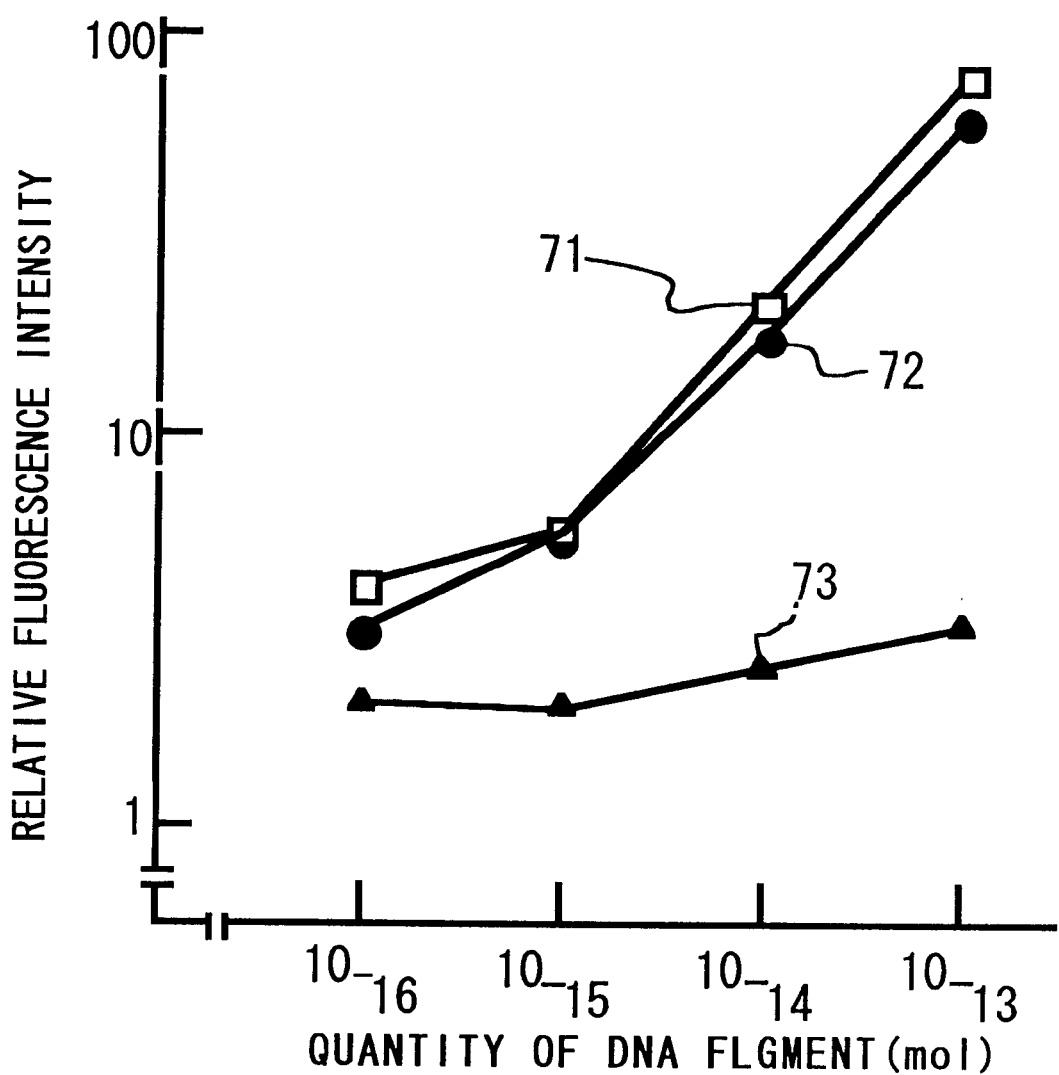

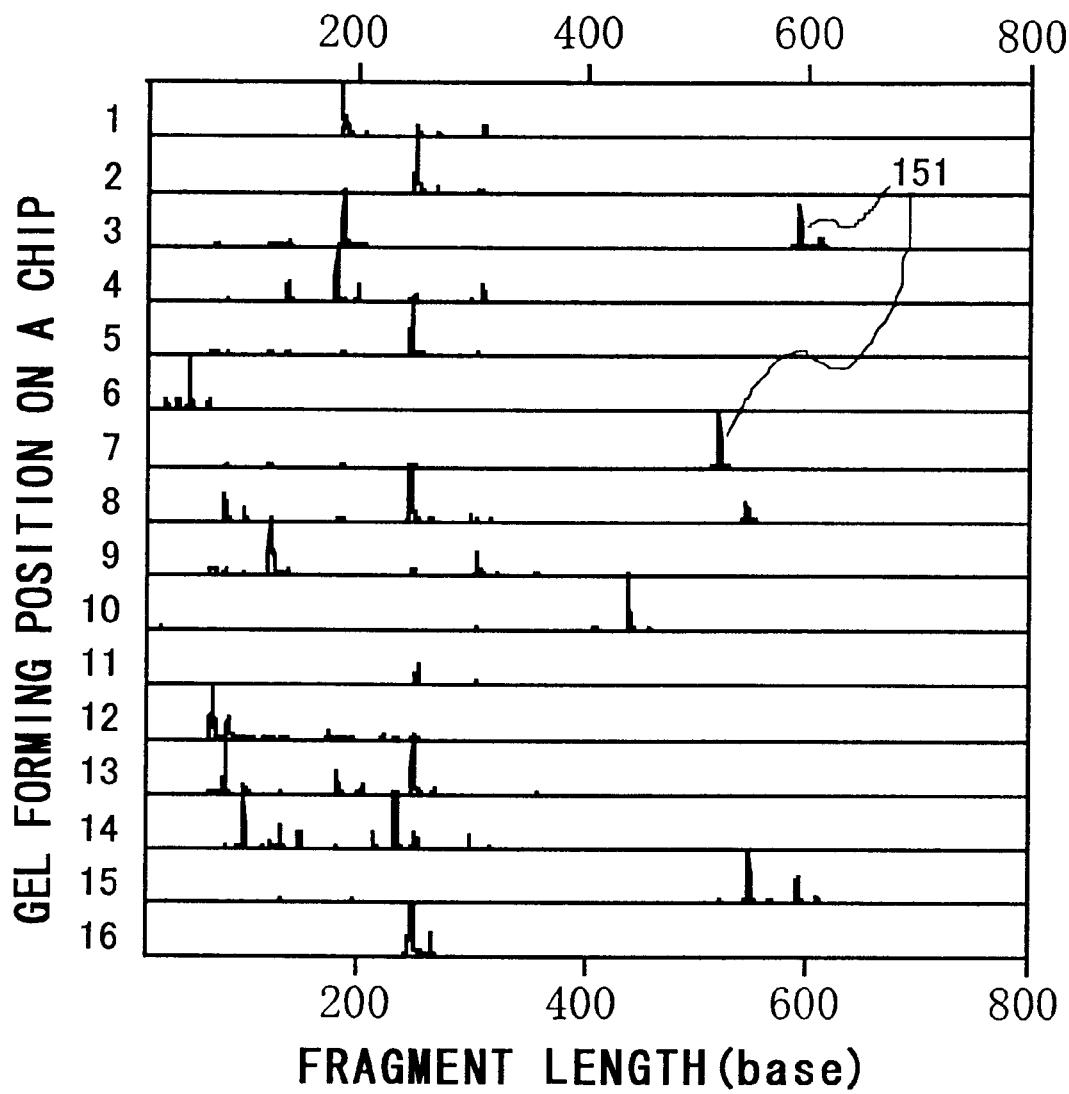

POLYNUCLEOTIDE PROBE CHIP AND POLYNUCLEOTIDE DETECTION METHOD

BACKGROUND OF THE INVENTION

The present invention relates to a probe chip for assaying various detection items about objects to be detected, such as DNA, RNA and proteins, at a time (i.e., a many item-detecting sensor), and in particular to a polynucleotide probe chip for assaying DNA and a polynucleotide detection method using the same.

The genome project rapidly approaches the stage of functional genomics. DNA analysis has been clarifying the mechanism of livings and living phenomena. And the DNA analysis has been used for diagnosis of the many diseases. It is effective for understanding living phenomena and examining the effect of genes that the situation of expression of the genes is examined. As a high-powered means, a DNA probe array or a DNA chip wherein a great deal of DNA probes are divided depending on each kind thereof and fixed on the surface of a solid starts to be used. As a method for preparing this DNA chip, there are known a method of using photochemical reaction and lithography, which is widely used in the semiconductor industry, to synthesize oligomers having a designed sequence, one base by one base, on many cells divided up to areas (prior art 1: Science 251, pp. 767–773 (1991)); a method of planting a DNA probe one by one in every area (prior art 2: Proc. Natl. Acad. Sci. USA 93, pp. 4913–4918 (1996)); and the like. In order to increase the amount of probes fixed on a chip, a method is contrived wherein an acrylamide gel film is formed on a chip and probes are fixed on this gel (prior art 2). As a method for fixing DNA probes used in a DNA probe chip, there are known a method of using the bonding of biotin and avidin or fixing DNA probes on the surface of gold (Au) through a SH residue (prior art 3: Biophysical Journal 71, pp. 1079–1086 (1996)); a method of fixing DNA probes on the surface of glass (prior art 4: Analytical Biochemistry 247, pp. 96–101 (1997)); a method of fixing DNA probes on an element matrix of acrylamide gel applied on the surface of glass (prior art 2), and the like.

SUMMARY OF THE INVENTION

Not only DNA or its derivative but also RNA or its derivative may be held on the surface of a chip. Therefore, a chip which holds any polynucleotide on its surface is referred to as a polynucleotide probe chip, hereinafter. In both of the prior arts 1 and 2, there remains problems that their methods for producing DNA chips require much labor and time and costs for the production are high, in particular a problem that the production of a DNA chip composed of minutes parts having closely formed probe arrays requires far more labor and time. That is, usual users cannot form the chip easily. In examination using a DNA chip, there generally arises a serious problem that kinetics of hybridization is slow since a target DNA in a solution needs to be associated with probes held on the surface of a narrow chip by bringing a large amount of the solution into contact with the probes. In the case that the target DNA is long for the probes, it is necessary that the DNA approaches the held probes along such a sequence direction that the DNA becomes complementary to the probes. Therefore, kinetics of hybridization is especially slow. Since the area of the surface of the chip is limited, the amount of the held probes is such an amount as represented by fmol and the amount is restrictive. Thus, there remains a problem that when a large amount of DNAs having highly similar sequences are present, the detection of a target DNA of a very small amount is frequently disturbed. In the case that the amount of probes is small, falsely positive hybridization, i.e., a phenomenon that the probes on the surface of a chip are occupied by DNA having highly similar sequences arise easily. Among the above-mentioned problems, the assay using the DNA chip in the prior arts 1 and 2 has the problem that much time is required and high sensitivity is not attained. The prior art 2 has the problem that the diffusion of a sample DNA into gel in a chip results in a rate-determining step of hybridization, and also has the problem that it is a skilled job and difficult for usual users to make a polynucleotide probe chip holding probes uniformly and having reproducibility by treating gels formed on the surface of the chips chemically in such a manner that the probes can bond to the gels. In order to detect simultaneously fluorescence from respective areas in chips in the prior art, it is necessary to apply a laser beam widened by an expander from the same face at the side of a camera. High output is also necessary since the density of the laser beam applied to the respective areas drops. The laser beam which is reflected on the chip surface and then directly projected onto a detector results in a background. Thus, detection with high sensitivity is difficult. In the case of using chips in the prior art, therefore, it is general to use a method of scanning a laser beam by means of a laser scanning microscopy. As a result, there arises a problem that much time is required for assay. Furthermore, it is difficult to separate DNA captured in each of areas in chips in the prior art, dependently on each of the areas, and collect the DNA, dependently on each of sizes of DNA.

In order to overcome the above-mentioned problems, an object of the present invention is to provide a method for producing a polynucleotide probe chip which makes it possible to form desired polynucleotide probes in a close state easily and is low in production costs. Another object of the present invention is to provide a low-priced polynucleotide probe chip which causes an improvement in the kinetics of hybridization on the surface of the chip, makes high-sensitivity assay for a short time possible, and makes falsely positive hybridization less; and a method for detecting polynucleotide(s) and a polynucleotide detecting device which make it possible to separate DNA captured in each of areas in a chip, dependently on each of the areas, and collect the DNA, dependently on each of sizes of the DNA.

The polynucleotide probe chip of the present invention wherein plural areas holding different polynucleotide probes are arranged has the following features.

(A) Gels hold the polynucleotide probes in the respective areas. A polynucleotide sample is migrated in the gels in the areas by electrophoresis to hybridize the polynucleotide probes of the gels with sample polynucleotides. Thus, the possibility that the polynucleotide probe chips collide with the sample polynucleotides are raised, so that the kinetics of hybridization is made higher and the amount of the probes held by the gels can be increased.

(B) In actual use, sample polynucleotides labelled with a fluorophore are added to the polynucleotide probe chip wherein the areas holding the different polynucleotide probes are arranged, and then the polynucleotide sample is migrated in the gels of the respective gels by electrophoresis to hybridize the polynucleotide probes in the gels with specific polynucleotides. The specific polynucleotides captured in the respective areas can be detected by detecting the fluorophore-labelled polynucleotides captured in the gels of the respective areas of the polynucleotide probe chip.

The sample polynucleotides are not labelled in advance. First, the sample polynucleotide samples are added to the polynucleotide probe chip, and then they are migrated in the gels in the areas by electrophoresis, to hybridize the polynucleotide probes in the gels with specific polynucleotides. Next, dNTP labelled with a fluorophore by extension reaction using DNA polymerase or ddNTP labelled with a fluorophore is introduced to the polynucleotide probes hybridized with the polynucleotides in the areas of the gels in the polynucleotide probe chip, so that the polynucleotides are labelled. In this way, the specific polynucleotides captured in the respective areas can be detected.

In order to detect a DNA (cDNA) fragment having an unknown base sequence as a sample, for example, in mRNA-expression-profile assay, there is used a polynucleotide probe chip holding polynucleotide probes comprising a combination of a portion of a substantially common base sequence having from a 10-base sequence to a 60-base sequence, and any 2-base sequence or 3-base sequence for recognizing the fragment at the 3' terminal thereof. Sample polynucleotides are added to the polynucleotide probe chip, and then they are migrated in the gels of the areas by electrophoresis, to hybridize the polynucleotide probes with the sample polynucleotides. Thus, hybrids are produced. The hybrids are detected by using DNA polymerase and introducing a fluorophore-labelled dNTP or a fluorophore-labelled ddNTP into the extended chains of the polynucleotide probes. Only the sample polynucleotide hybridized with the recognizing 2-base sequence or 3-base sequence at the 3' terminal of the polynucleotide probes is detected by the existence of the fluorescence label. Alternatively, the complementary chain of the sample polynucleotide hybridized with the polynucleotide probe is synthesized by using the polynucleotide probe as a primer. The chain is modified to obtain an extended complementary chain composed of one chain. Next, this chain is hybridized with a fluorophore-labelled probe complementary to the extended complementary chain, and then the existence and the kind of hybridized sample are detected.

(C) A structure wherein electrodes are arranged in the chip makes it possible to migrate the sample polynucleotides in the gels, holding the polynucleotide probes, in the respective areas to hybridize the polynucleotide probes in the gels with the sample polynucleotides. In order to raise the kinetics of the hybridization to improve the efficiency of capturing specific polynucleotides, the sample polynucleotides are migrated in the same gels plural times to improve the efficiency of the hybridization.

(D) A polynucleotide probe chip wherein elements for detecting light are arranged or formed in respective areas of the surface of a substrate of the chip is used, and respective gels in the areas are irradiated along the direction parallel to the substrate surface with laser light. In this way, fluorescence from the gels in the areas can be simultaneously detected. This polynucleotide probe chip has the substrate on which a fine photodiode array is formed. Metallic vaporized layers through which light having a specific wavelength range transmits (fluorescence emitted from a fluorescence label) are formed on the respective photodiodes, and transparent electrodes are formed on the metallic vaporized layers through insulating layers. DNA probes are fixed onto the surfaces of the transparent electrodes. Wiring for detecting electric currents flowing through the respective photodiodes is formed on the surface of the polynucleotide probe chip. A reflective plate having a reflective face is pushed onto the upper surface of the polynucleotide probe chip in the manner that laser light is totally reflected. In the state that the reflective plate is pushed onto the gel surface in the respective areas, laser light is radiated thereto. Therefore, the laser light advances with total reflection being repeated, and is radiated along the direction substantially parallel to the substrate surface to the gels in the respective areas.

(E) A method for producing the polynucleotide probe chip is as follows. A monomer having a reaction residue and a probe set comprising plural kinds of polynucleotide probes having a residue bonded to the reaction residue of the monomer, and a chip comprising plural areas are beforehand prepared. Each kind of any probes selected from the polynucleotide probe set is mixed with the monomer, and the mixture is added to each of the different areas and gelatinized. By such a preparation, polynucleotide probes of a custom design can be held. As the monomer, acrylamide and derivatives thereof can be used. As the polynucleotide probes having a residue bonded to the reaction residue of the monomer, polynucleotide probes having an active vinyl residue such as an acryl residue can be used.

Of course, the polynucleotide probe held in each of the area is not limited to one kind. According to the purpose of analysis, a combination of plural kinds of the probes is held in each of the areas. A monomer having a reaction residue and a probe set comprising plural kinds of polynucleotide probes having a residue bonded to the reaction residue of the monomer, and a chip comprising plural areas are beforehand prepared. Each kind of any probes selected from the polynucleotide probe set is mixed with the monomer, and the mixture is added to each of the different areas and gelatinized. By such a preparation, polynucleotide probes of a custom design can be prepared. If such a producing method is used, a constant volume of the probes is beforehand handled in the state of liquid and is held in the gel. Therefore, a polynucleotide probe chip which is uniform and is high in reproducibility can be produced. The method that the polynucleotide probes of the present invention are held by the polynucleotide probe chip is entirely different from that of the prior arts 2, 3 and 4.

According to the present invention, a polynucleotide probe of kind necessary for use can easily be arranged in the polynucleotide probe chip. The respective polynucleotide probes having a residue bonded to the reaction residue of the monomer can be prepared only by reacting polynucleotide having an amino residue and prepared in a DNA synthesizing device, N-acryloxysuccinimide, allylglycidyl ether and acrolein, and collecting the reactant product by gel filtration or ethanol precipitation. Thus, the probes are low-priced, and the polynucleotide probe chip itself can also be produced at a low price. The respective polynucleotide probes can be preserved.

According to the present invention, a probe array holding any kind of probe can easily be produced at a low-priced. Moreover, the DNA probes held in the gels and electrophoresis are used to migrate the sample in the gels forcibly. Accordingly, the probes held in the gels can be hybridized quickly and effectively with the sample DNA fragments. Since the DNA fragments which are not hybridized can be removed by electrophoresis, a background can be made lower by the present invention than by chips using gels in the prior art. In the present invention, the gels in all of the small holes (or each row of the small holes), or the gels on the surface of respective areas constituting a row can be simultaneously irradiated, from the side face of the chip, with light. Therefore, the time for scanning is unnecessary. Laser light is radiated in the direction that fluorescence is detected and in the direction perpendicular thereto. This is an arrangement that scatting light is not directly projected into a detector. The light emitted from the respective small holes can be simultaneously detected with a two-dimensional camera. Thus, assay with high-speed and high-sensitivity can be made. Furthermore, the respective holes (or the respective areas) can be irradiated simultaneously and effectively even by means of a sub-milliwatt class semiconductor laser.

An aspect of the present invention can be summarized as follows. Prepared are a monomer having a reaction residue and a polynucleotide probe set comprising plural kinds of polynucleotide probes having a residue bonded to the reaction residue. The monomer is mixed with each kind of polynucleotide probes comprising any plural probes selected from the polynucleotide probe set. Each kind of the resultant mixtures is added to each of different small holes to gelatinize the mixture. Thus, a polynucleotide probe chip is produced. Sample DNA is forcibly migrated in the gels by electrophoresis. Laser light is projected onto the side face of the chip. The fluorescence emitted from the whole surface of the chip is collectively detected with a high-sensitive two-dimensional detector. Thus, it is possible to provide the polynucleotide probe chip for detecting DNA and the assay method, which have high hybridization-efficiency and make high-sensitivity and high-speed DNA detection possible.

BRIEF DESCRIPTION OF THE DRAWINGS

FIG. 7 is a graph showing a line for assaying the amount of the DNA fragments with the polynucleotide probe chip of the first embodiment according to the present invention.

FIG. 15 is a view showing an example of the electrophoresis pattern obtaining by collecting DNA fragments hybridized with respective areas of a polynucleotide probe chip from the areas and measuring them.

DESCRIPTION OF THE PREFERRED EMBODIMENTS

Figure 1A:
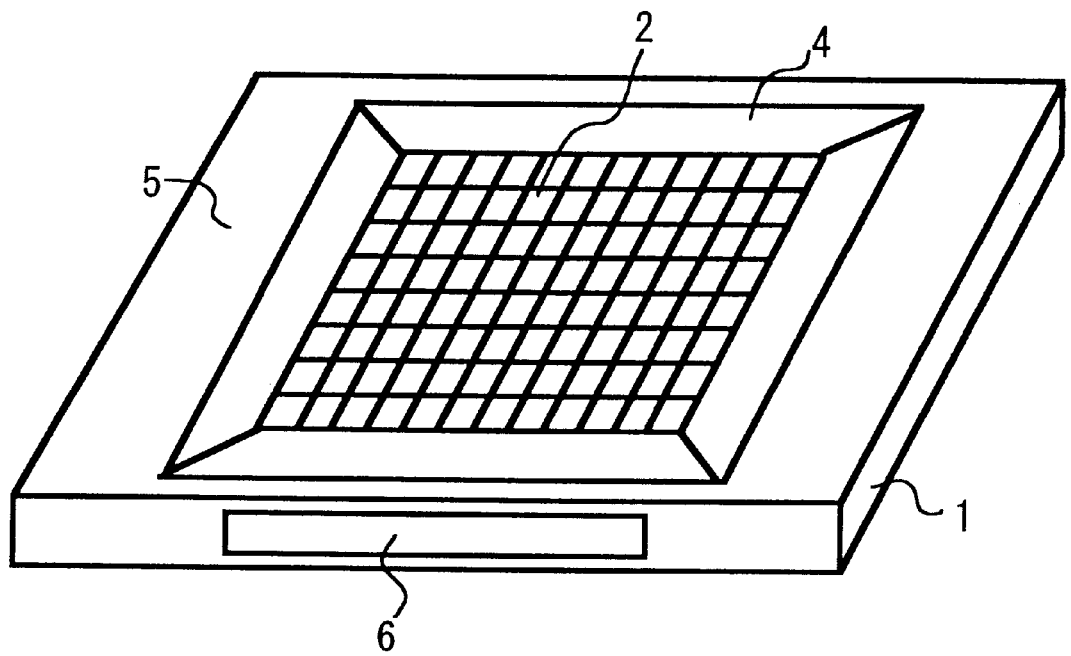
FIG. 1A is a perspective view of an example of the polynucleotide probe chip of the present invention.

Referring to the drawings, the present invention will be described in detail by way of embodiments, hereinafter.

First Embodiment

Figure 1B:
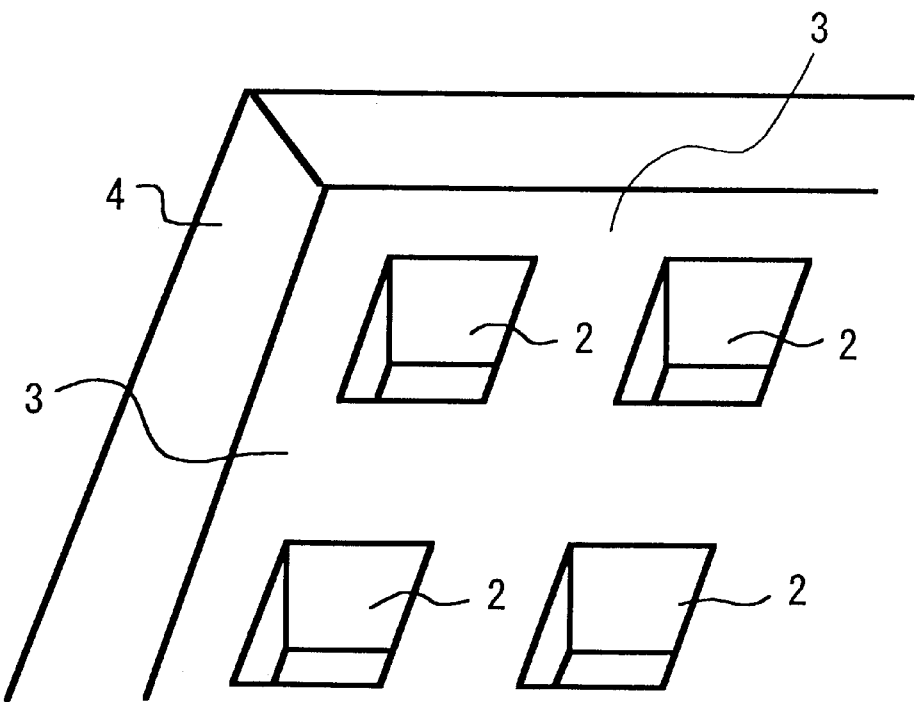
FIG. 1B is a partially enlarged view of FIG. 1A.

FIGS. 1A and 1B illustrate an example of the polynucleotide probe chip according to the present invention. FIG. 1A is a perspective view of the polynucleotide probe chip, and FIG. 1B is a partially enlarged view of the chip. The polynucleotide probe chip 1 is made of a plastic. A concave portion which is surrounded by a hydrophobic portion 5 whose surface is subjected to hydrophobic treatment and which has a flat base face is formed, and further plural small holes (areas where small holes are formed) 2 having upper and lower open ends are arranged in the form of cross stripes and formed in the base face of the concave portion. A hydrophilic portion 4 whose surface is subjected to hydrophilic treatment is formed between the hydrophobic portion 4 and the base face of the concave portion. The upper opening of the small holes 2 is an opening 0.5 mm square. The distance between the upper and lower openings is 1 mm. The shape of the opening of the small holes 2 is not limited to the square, and may be any shape such as a rectangle or a circle. The small holes 2 are arranged in the X and Y directions through a barrier 3 to constitute a 16×16 matrix. In other words, the centers of the small holes 2 are two-dimensionally arranged at intervals of 1 mm.

The area of the upper opening of the small holes 2 is smaller than that of the lower openings thereof, to make it possible to hold a gel. That is, the small holes 2 are tapered from their upper opening to their lower opening so that a gel can easily be held at the time of producing the gel. The hydrophobic portion 5 and the hydrophilic portion 4 make it possible to hold the sample solution easily in the concave portion having the small holes 2 in which the gel is held.

Figure 6:
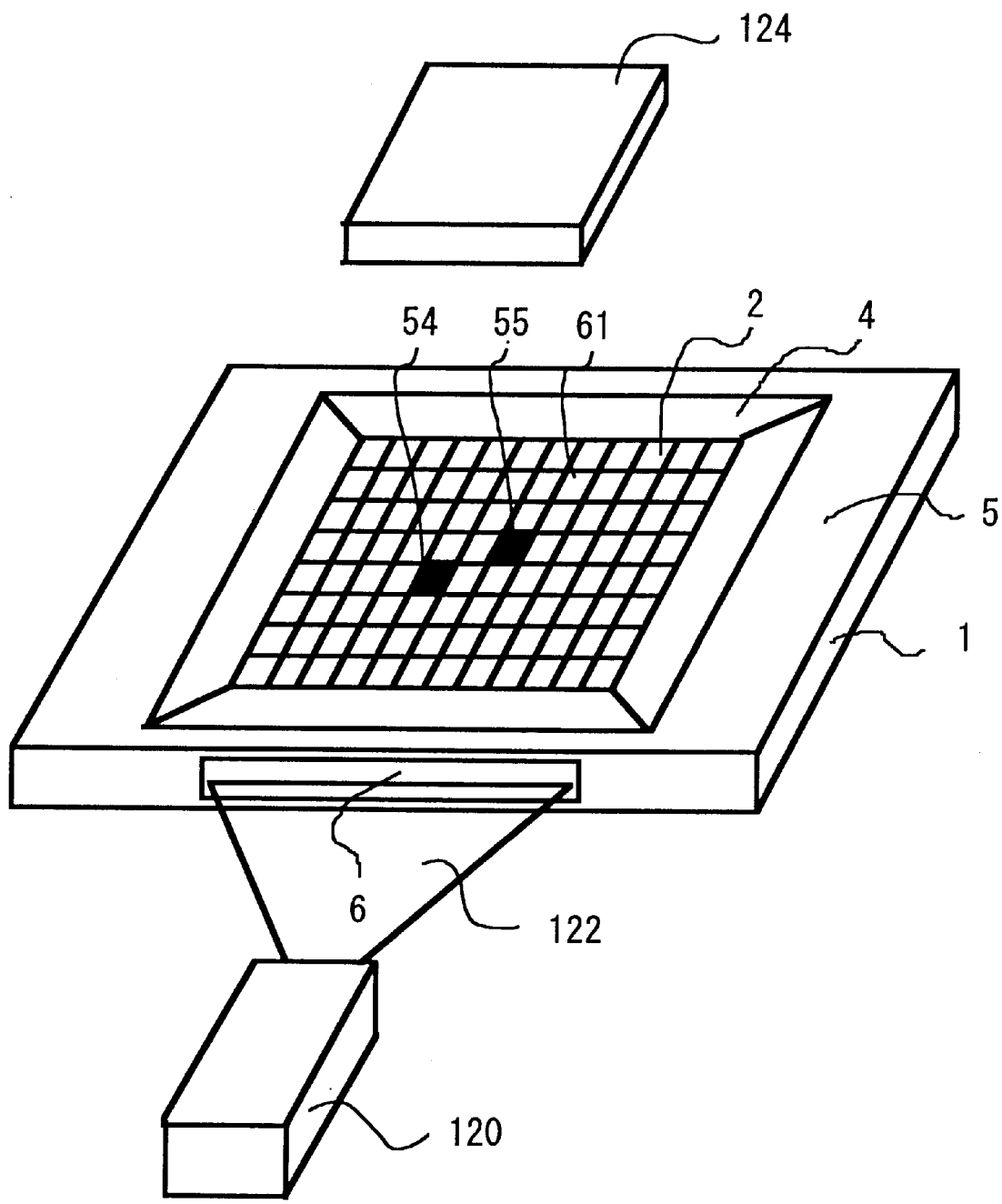
FIG. 6 is a view showing the position of fluorophore-labelled DNA fragments detected on the polynucleotide probe chip in the first embodiment according to the present invention.

A laser light introducing portion 6 for introducing laser light, which is optically polished, is formed at the side face of the polynucleotide probe chip. The side of the respective small holes 2 is irradiated with laser light. A material of the plastic, there is used optically transparent poly (methylmethacrylate) (PMMA), through which laser light having a wavelength of 400 to 650 nm transmits. A laser source for obtaining laser light and a high sensitive cooled CCD camera for detecting fluorescence emitted from a fluorescence label, which are not illustrated in FIG. 1A, are illustrated in FIG. 6.

The following will describe the surface treatment of the inner wall of the respective small holes 2 (the side face of the small holes 2). In order to hold a gel inside the small holes 2 surely when the gel is produced inside of the small holes 2, the inner wall of the small holes 2 is made into an uneven form of a molecular level by etching based on oxygen plasma.

Figure 2:
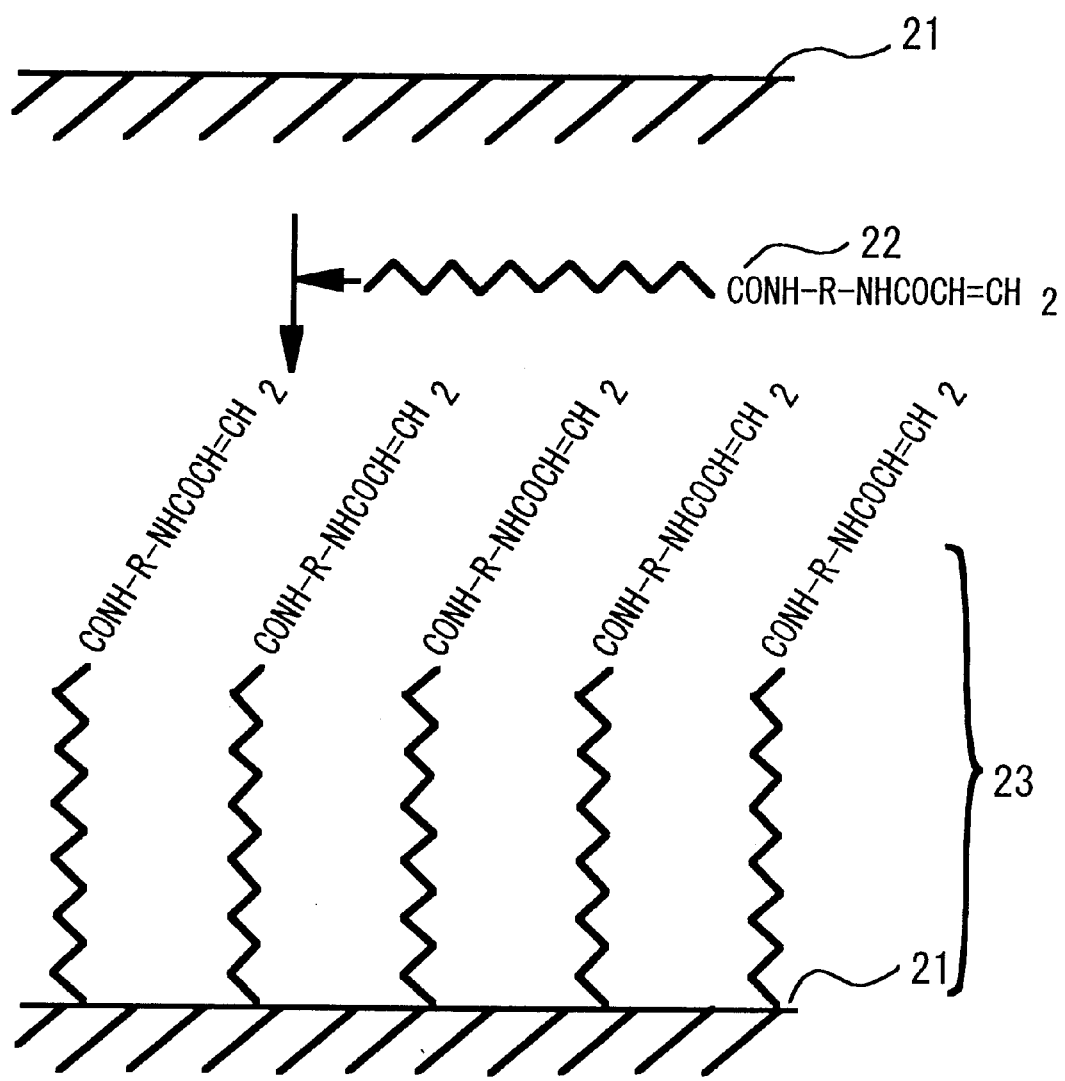
FIG. 2 is a view for explaining surface treatment of the inner wall of a small hole holding a gel of the polynucleotide probe chip of a first embodiment according to the present invention.

FIG. 2 is a view for explaining the surface treatment of the inner wall of the small holes in which the gel of the polynucleotide probe chip is held. A reagent 22 having an acryl residue at a part of a chain aliphatic compound is applied to the inner wall 21 of the respective small holes 2 (the side face of the small holes 2) to obtain a state 23 showing the active acrylic residue on the inner wall 21 of the small holes 2. In the first embodiment, the acrylamide gel is held in each of the small holes 2. At this time, the acryl residue and the acrylamide gel are connected with each other on the inner wall 21 of the small holes 2. The reagent 22 is not chemically bonded directly to the surface of the plastic, but the reagent 22 is fixed on the surface of the plastic by hydrophobic bonding of the intermolecular chain aliphatic moiety of the reagent 22.

Figure 3:
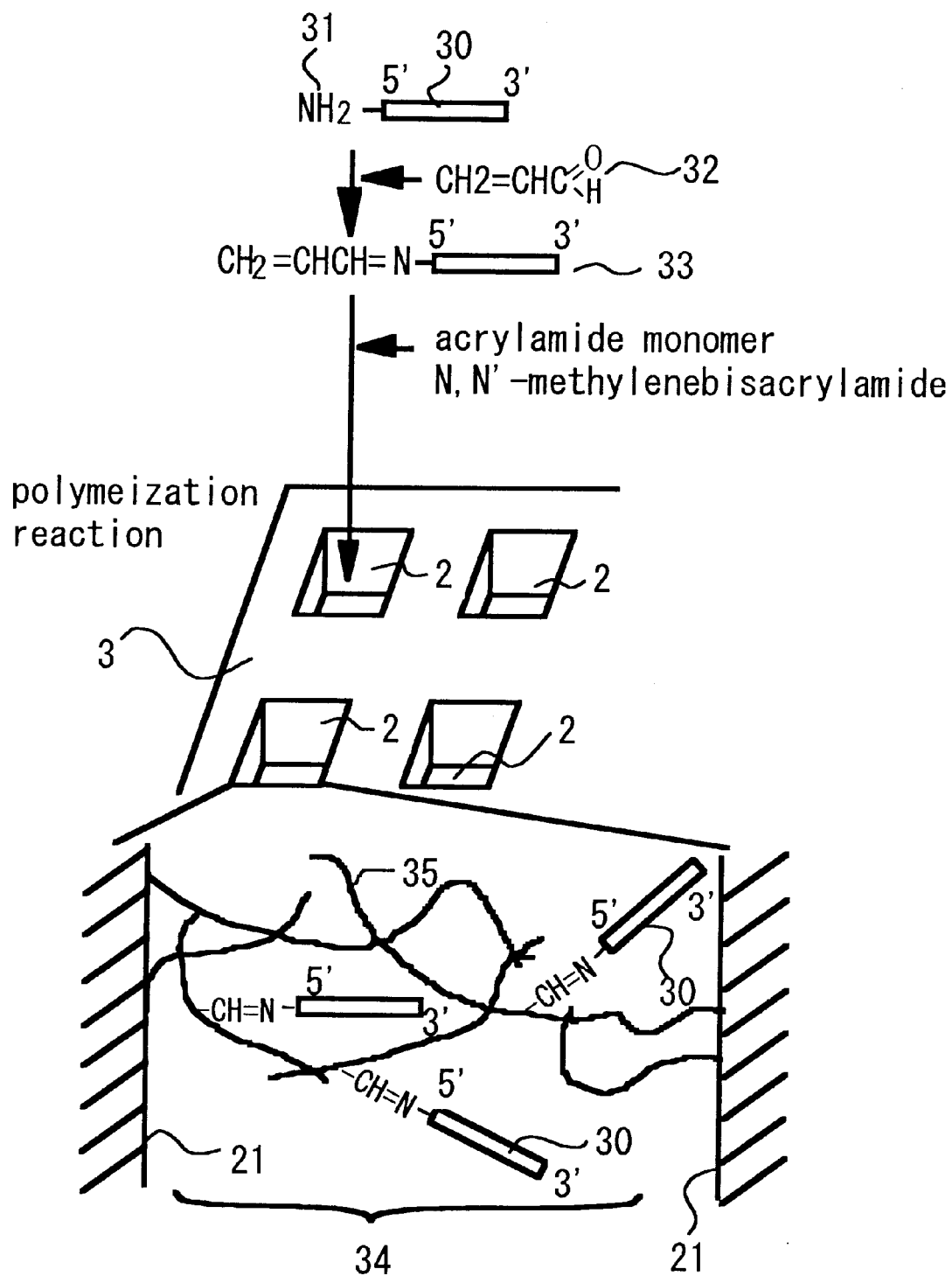
FIG. 3 is a view for explaining a method for holding the polynucleotide probe on the polynucleotide probe chip of the first embodiment according to the present invention.

FIG. 3 is a view for explaining a method for causing the polynucleotide probe chips to hold polynucleotide probes. 256 kinds of probes, which are different from each other, are prepared. Respective polynucleotide probes 30 having an amino residue 31 at the 5' terminal are synthesized by the phosphoamidite method. These probes 30 are used. Acrolein 32 is mixed with an aqueous solution of 10 µM of the respective probes so that the concentration of the acrolein 32 is made up to 2 mM. The mixture is reacted at 20° C. for 30 minutes and then an unreacted acrolein is removed by gel filtration through Sephadex G25. By this operation, the amino residue 31 of the polynucleotide probes 30 is reacted with the aldehyde residue of the acrolein 32 to obtain polynucleotide probes 33 having an active acryl residue at the 5' terminal. They are dried in a vacuum and then the polynucleotide probes having an acryl residue at the 5' terminal are preserved, in the state of an aqueous solution having a concentration of 10 µM of the probes, at −20° C. in the atmosphere of helium.

As a gel precursor, there is used a mixture solution of acrylamide monomer and N,N'-methylenebisacrylamide (39:1). To a mixture solution of 2.5 µL of 1.5M Tris hydrochloric acid buffer (pH 8.5), containing 0.015% ammonium persulfate, 0.5 µL of the polynucleotide probes (10 µM) having an acryl residue, and 1.5 µL of 15% acrylamide is added 0.5 µL of N,N,N',N'-tetramethylethylenediamine (40 nM). Immediately, the solution is dropwise added in the small holes 2. The reaction for the polymerization is conducted in the atmosphere of helium.

In radical polymerizing reaction, the polymerization is blocked by oxygen, or the plastic surface itself. In order to prevent the blocking of the polymerization and generation of bubbles in fine portions, the polymerization is conducted in the atmosphere of helium. The blocking of the polymerization cannot be completely prevented by helium-replacement. However, since the small holes 2 are tapered, the small holes 2 can hold a gel surely. This is because the helium-replacement makes it possible to prevent bubbles from being generated in the small holes.

Some amount of the reactant solution is charged into the small holes 2 by a capillary phenomenon. The polynucleotide probe chip can be effectively obtained by preparing the solutions except N,N,N',N'-tetramethylethylenediamine for all of the probes, adding N,N,N',N'-tetramethylethylenediamine to the respective solutions, and immediately adding the respective probes in the respective small holes 2. Alternatively, the reagents other than N,N,N',N'-tetramethylethylenediamine, that is, a solution wherein the Tris buffer containing acrylamide, N,N'-methylenebisacrylamide and ammonium persulfate are mixed with the polynucleotide probes having an acryl residue is prepared, and then this solution is dropwise added to the surface of the polynucleotide probe chip to charge the solution into the small holes. Subsequently, the polynucleotide probe chip is exposed to gasified or misted N,N,N',N'-tetramethylethylenediamine so as to start polymerization reaction. Thus, the polynucleotide probe chip can easily be produced. In the above-mentioned manner, the polynucleotide probes 30 can be fixed to polyacrylamide gel strands (gel matrix) 35, as shown by reference number 34. The polyacrylamide gel strands (gel matrix) 35 are fixed onto the inner wall 21 of the small holes 2 (the side of the small holes).

Figure 4:
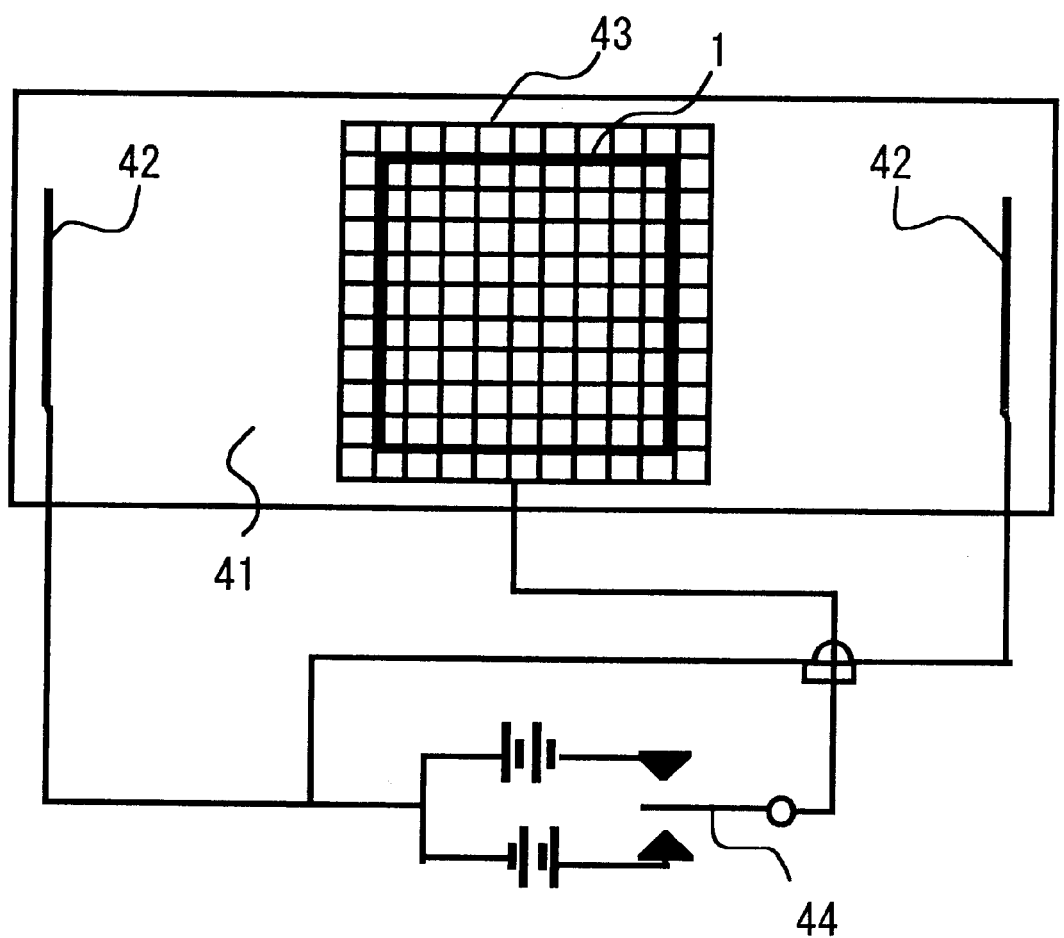
FIG. 4 is a plane view showing the positional relationship between the polynucleotide probe chip of the first embodiment according to the present invention and electrophoresis electrodes.

FIG. 4 is a plan view illustrating the positional relationship between the polynucleotide probe chip and electrophoresis electrodes. As illustrated in FIG. 4, the lower face of the polynucleotide probe chip 1 (at the side of the lower opening of the small holes 2) is set inside an electrode vessel 41 in which electrodes 42 are located. An electrode 43 in a mesh form is set to the surface of the sample solution (or in the sample solution) added onto the upper face of the polynucleotide probe chip 1 (the side of the upper opening of the small holes 2). Polarities are selected with a switch 44 for switching polarities, to apply voltage between the electrodes 42 and 43.

The following will describe an example wherein the produced polynucleotide probe chip is used to assay various DNA fragments actually. In the first embodiment, the sequence having CATG in 8.7 kb of a human DNA clone is recognized with a restriction enzyme Hsp92II (4-base recognizing enzyme), and cut at the 3'-protrude end of the 4 base sequence having CATG with the restriction enzyme, to obtain a group of fragments (referred to as an 8.7 kb DNA fragment group, hereinafter). The first embodiment demonstrates that the group of the fragments is used so that various fragments can be separately detected from the fragment group. This embodiment will describe an example in which probes of the following sequence Nos. 1 and 2 are used to detect DNA fragments complementary to the probes of sequence Nos. 1 and 2.

5'-TCTCACACCAGCTGTCCCAAGAC
CGTTTGC-3'          Prove of sequence No. 1:

5'-AATACAGGCATCCTTCACTACATT
TTCCCT-3'           Probe of sequence No. 2:

The probes of sequence Nos. 1 and 2 are held inside the different small holes 2 of the polynucleotide probe chip. Probes which are not complementarily bonded to the 8.7 kb DNA fragment group are held inside the other small holes 2. The validity of the polynucleotide probe chip is checked by examining whether or not only complementary fragments to the probes of sequence Nos. 1 and 2 can be detected from a mixture. A specific example will be described hereinafter.

Preparation of a Sample

A human DNA clone (8.7 kb) is cut with a restriction enzyme and then a DNA adapter sequence having a sequence of No. 3 is bonded to the 3' terminal of the cut clone, to prepare a DNA fragment mixture 52 as a model sample. First, the DNA (8.7 kb) is cut with the restriction enzyme Hsp92II and then DNA having a known sequence of sequence No. 3 at the 3' terminal and labelled with a fluorophore (sulforhodamine 101 (SR101)) is linked to both the 3' terminals of the resultant fragment with DNA ligase. DNA of sequence No. 3 (adapter):

5'-ACTGGCCGTCGTTT-3'

A phosphoric residue for ligation reaction is bonded to the 5' terminal of the DNA (adapter) of sequence No. 3. That is, 400 fmol of a human DNA clone is dissolved into 10 nM of Tris-HCl solution (pH 7.4) containing 10 nM of $MgCl_2$ and 15 μM of KCl, and then 40 units of Hsp92II (Promega, UK) is added thereto. The solution is reacted at 37° C. for 2 hours to cut the clone completely. After the DNA is precipitated with ethanol to be collected, the phosphoric residue of the 5' terminal is removed with alkaline phosphotase. The adapter (20 pmol) of sequence No. 3, the 3' terminal of which is labelled with the fluorophore and which has a phosphoric residue at the 5' terminal, and DNA (helper oligomer) (20 pmol) having a known sequence of sequence No. 4, which can be complementarily bonded to the DNA of sequence No. 3, are added to 400 fmol of the cut DNA fragment mixture, so that the amount of the resultant is made up to 40 μL. Next, 20 μL of Ligation High (manufactured by TOYOBO) are added thereto and then ligation reaction is conducted at 16° C. for 1 hour. DNA OF sequence No. 4 (helper oligomer):

5'-AAACGACGGCCAGTCATC-3'

The 3' terminal of the DNA of sequence No. 3 (helper oligomer) is phosphorylated. In this way, the adapter sequence is introduced to only the 3' terminal of the respective DNA fragments, and simultaneously the 3' terminal thereof is labelled with the fluorophore 53 (sulforhodamine 101).

The ligation reaction is a reaction for linking the OH residue of the 3' terminal of the DNA fragments to the phosphoric residue of the 5' terminal of the DNA of sequence No. 3. In the method described herein, ligation between the DNA of sequence No. 3 and the DNA of sequence No. 4 is suppressed since the 3' terminal of the DNA of sequence No. 4 is modified with the phosphoric residue. Moreover, the DNA fragments are prevented from being re-bonded to each other since the phosphoric residue of the 5' terminal of the DNA fragments is removed. For these reasons, the DNA of sequence No. 3 can surely be introduced. The thus prepared fluorophore-labelled DNA fragment mixture 52 is diluted to prepare samples of various concentrations of 0–1 nM.

The following will describe detection of DNA fragments by means of the polynucleotide probe chip. To the polynucleotide probe chip were dropwise added 250 μL of the sample solution, so that a liquid phase of about 2 mm in thickness is produced.

An electrical potential of 20 V is applied to the electrode 42, as an anode, and the electrode 43, as a cathode. After 10 seconds, the polarity is reversed and a reversed electrical potential is applied for 10 seconds. This cycle is repeated 10 times to hybridize the DNA fragments with the polynucleotide probes wherein the gels are held in the respective small holes. Next, an electrical potential of 20 V is applied to the electrode 42, as an anode, and the electrode 43, as a cathode, to remove the DNA fragments which are not hybridized.

Figure 5:
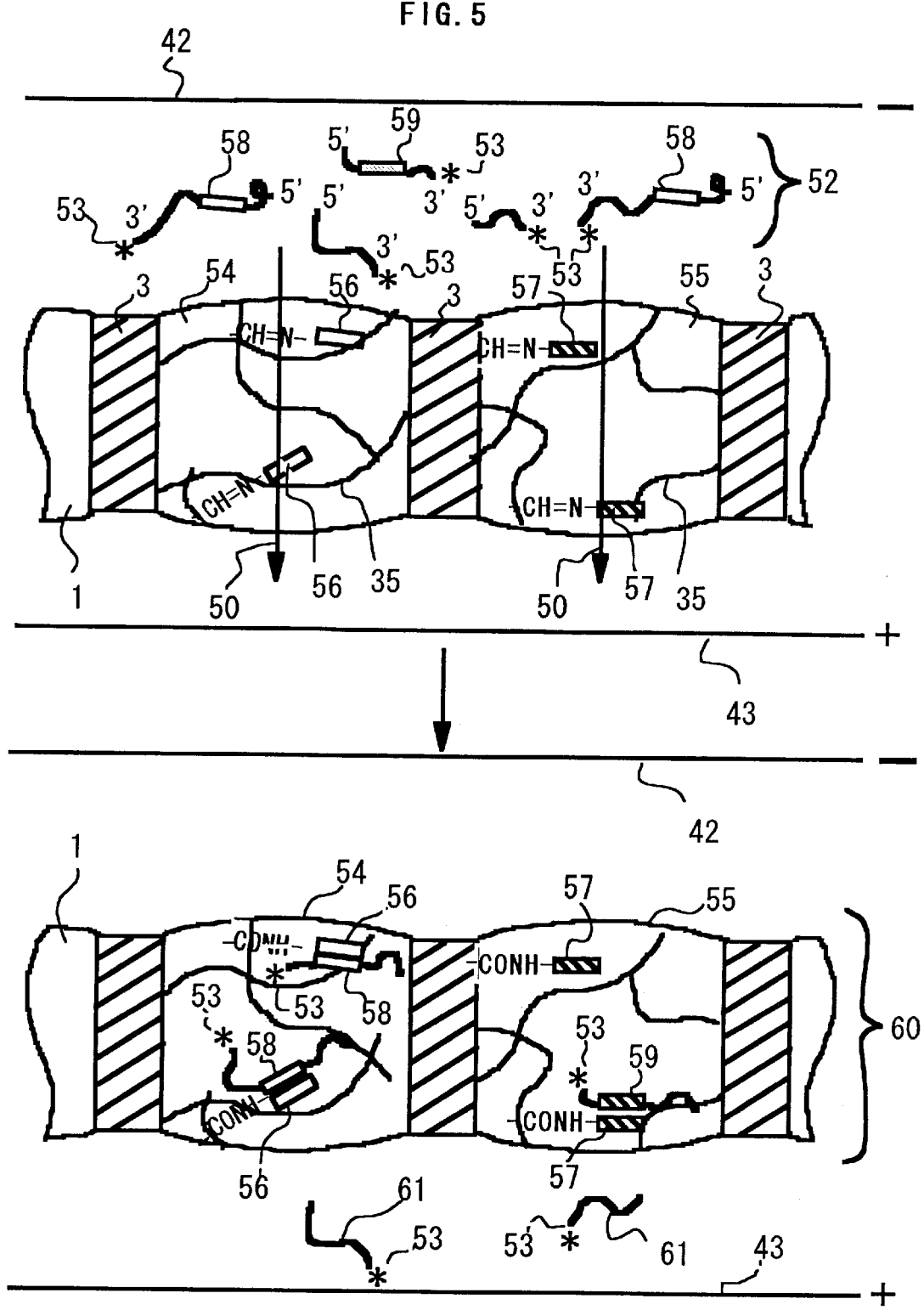
FIG. 5 is a view for explaining the action of the polynucleotide probe chip of the first embodiment according to the present invention.

FIG. 5 is a view for explaining the action of the polynucleotide probe chip shown in FIGS. 1A and 1B. Straight lines 50 having an arrow represent an electrophoresis direction along which the fluorophore-labelled DNA fragment mixture 52 is migrated by electrophoresis. The polynucleotide probe 56 (the probe of sequence No. 1) and that 57 (the probe of sequence No. 2) which are different from each other are fixed onto the small holes 54 and 55 which are divided with the barrier 3. When the fluorophore-labelled DNA fragment mixture 52 passes through the polyacrylamide gels, the fluorophore-labelled DNA fragment having the base sequence 58 complementary to the polynucleotide probe 56 is captured in the small hole 54 and the fluorophore-labelled DNA fragment having the base sequence 59 complementary to the polynucleotide probe 57 is captured in the small hole 55, as shown by reference number 60. The other fluorophore labelled DNA fragments 61 are not captured in the small holes 54 or 55 and pass through the small holes.

The optically polished face of the polynucleotide probe chip in which the reaction has finished (the laser light introducing portion 6 in FIG. 1A) is irradiated with He—Ne laser light having a wavelength of 594 nm. The laser light may be scanned to be radiated, or may be widened to be radiated at a time. The laser light is applied to each of the small holes 2. The fluorescence emitted from the fluorophore 53 (sulforhodamine 101) is measured with a high sensitive cooled CCD from the upper or lower face of the polynucleotide probe chip through a vapor deposited filter through which light having a wavelength of 605 to 660 nm transmits.

FIG. 6 is a view illustrating positions of the fluorophore-labelled DNA fragments detected on the polynucleotide probe chip. As illustrated in FIG. 6, fluorescence can be detected at the small holes 54 and 55 inside which the probe 56 of sequence No. 1 and the probe 57 of sequence No. 2 are held, respectively. At the small holes 61, to which other probes than the probes 56 and 57 are fixed, only fluorescence having 1/20 or less of the fluorescence intensity detected at the small holes 54 and 55 is detected. FIG. 6 illustrates a laser source 120 for emitting laser light 122, and a high sensitive cooled CCD 124, both of which are not illustrated in FIG. 1A.

FIG. 7 is a graph showing a line for assaying the amount of the DNA fragments with the polynucleotide probe chip. FIG. 7 is obtained by measuring fluorescence intensities to various concentrations of the DNA fragments. Reference number 71, 72 and 73 represent the fluorescence intensity (relative intensity) obtained from the small hole 54 inside which the probe 56 of sequence No. 1 is held, the fluorescence intensity (relative intensity) obtained from the small hole 55 inside which the probe 57 of sequence No. 2 is held, and the fluorescence intensity obtained from the position of the small hole 61 (i.e., the fluorescence intensity originated from background generated by non-specific adsorption), respectively.

Second Embodiment

Another form of the polynucleotide probe chip of the present invention will be described, hereinafter. In the polynucleotide prove chip through which small holes penetrate in the up and down direction, according to the first embodiment, it is easy to produce a gel which holds a polynucleotide probe in each of the small holes. However, it is necessary to provide separately an electrode for migrating the added polynucleotide sample in the gel in each of the areas by electrophoresis. In the second embodiment, such an electrode is formed on a substrate.

Figure 8A:
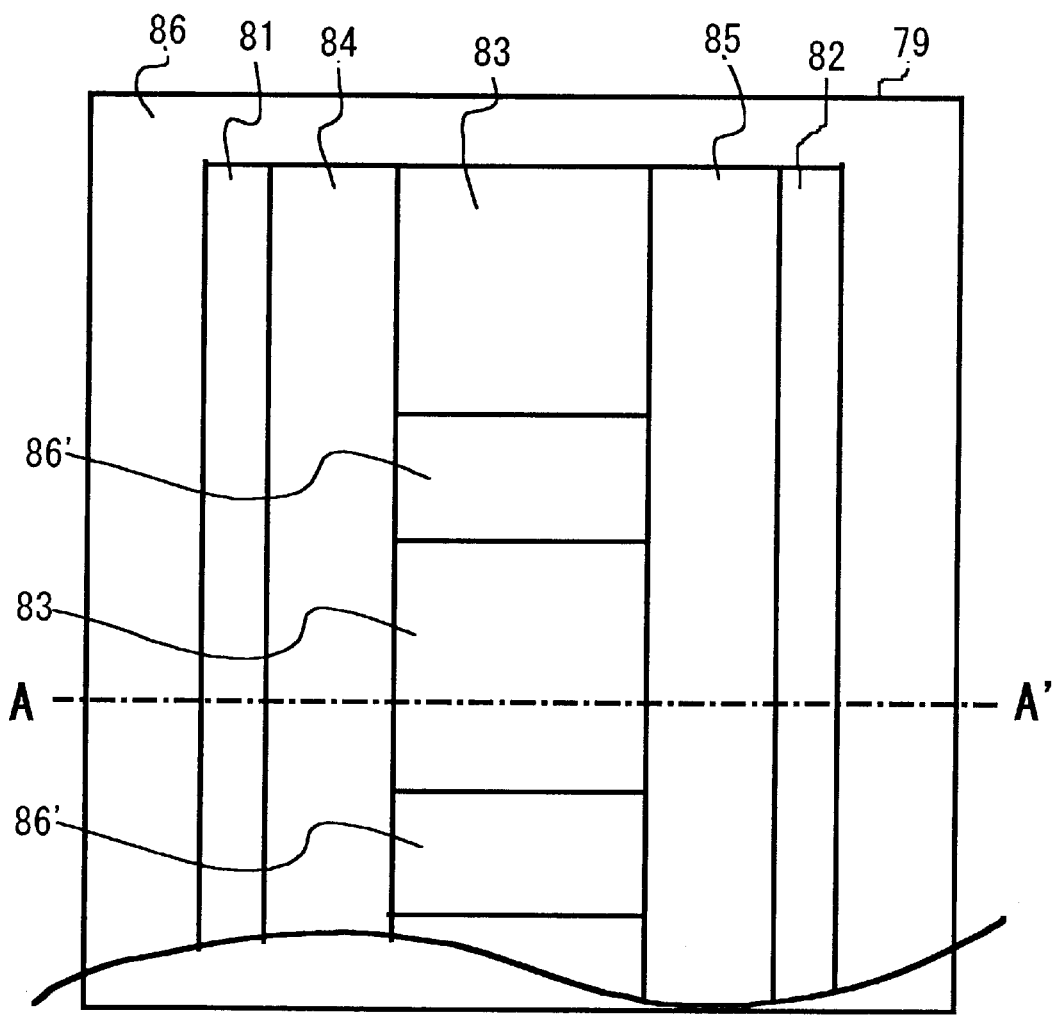
FIG. 8A is a plane view illustrating the structure of the polynucleotide probe chip of a second embodiment according to the present invention.
Figure 8B:
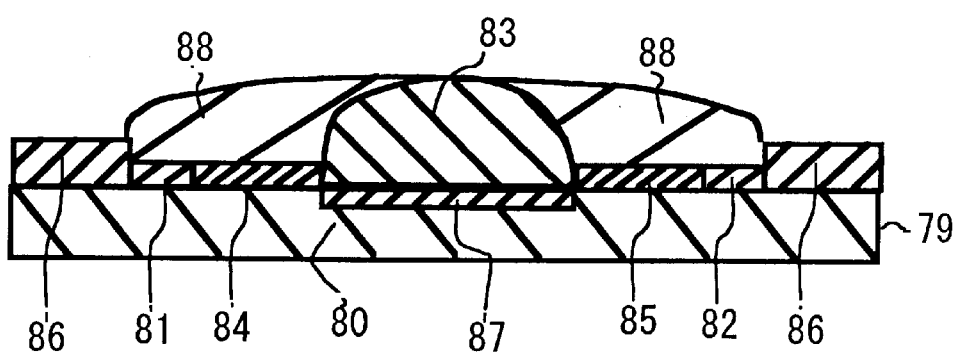
FIG. 8B is a cross section illustrating the structure of the polynucleotide probe chip of the second embodiment according to the present invention.

FIG. 8A is a plane view of a polynucleotide probe chip 79 of the second embodiment, and FIG. 8B is a sectional view taken along A–A' line of FIG. 8A. The polynucleotide probe chip 79 has, on a glass substrate 80, a concave portion whose surface is composed of a hydrophobic member (hydrophobic portion 86), and also has gels 83 holding polynucleotide probes, which are partitioned along one direction within the concave portion by hydrophobic portions 86' whose surface is hydrophobic, and linear electrodes 81 and 82 and hydrophilic portions 84 and 85, between which the gel 83 is arranged along one direction within the concave portion. The electrodes 81 and 82, the hydrophilic portions 84 and 85, areas 87 wherein the gel is produced, and the hydrophobic portions 86' are on substantially the same plane. The areas 87 wherein the gel is produced are isolated by the hydrophobic portions 86 and 86'. The number of the located areas 87 is, for example, 16.

An optically polished laser light introducing portion 6 (not shown in FIGS. 8A or 8B) for introducing laser light which is radiated to the gels 83 is formed in the member whose surface is hydrophobic (the hydrophobic portions 86') in the same manner as in the first embodiment. In the case that the concave portion having a flat base face is directly formed in the glass substrate 80, the surface of the glass substrate is optically polished to form the laser light introducing portion.

The size of the respective areas 87 is 0.5 mm×0.5 mm. The length perpendicular to the A–A' direction of the hydrophobic portions 86' is 0.25 mm, and the length along the A–A' direction of the hydrophilic portions 84 and 85 is 0.25 mm. The length along the A–A' direction of the electrodes 81 and 82 is 0.15 mm. That is, the centers of the 16 areas are one-dimensionally arranged at intervals of 0.75 mm.

Methacryloxypropyltrimethoxysilane is applied to the areas 87 wherein the gel is produced in the glass substrate 80. It is baked at 120° C. for 30 minutes to introduce residues having a double bond to the surface. By evaporating gold, the electrodes 81 and 82 are formed on the surface of the glass substrate 80. The hydrophobic portions 86 are formed by evaporating Teflon. In the hydrophilic portions 84 and 85, Teflon is first evaporated.

In the same manner as in the first embodiment, the gel holding the polynucleotide probe is produced in the areas 87 having a residue having a double bond. That is, as a gel precursor, there is used a mixture solution of acrylamide monomer and N,N'-methylenebisacrylamide (29:1). To a mixture solution of 2.5 μL of 1.5M Tris hydrochloric acid buffer (pH 8.5), containing 0.015% ammonium persulfate, 0.5 μL of the polynucleotide probes (0.2 nM) having the acryl residue, and 0.5 μL of 15% acrylamide is added 0.5 μL of N,N,N',N'-tetramethylethylenediamine (40 nM). The solutions except N,N,N',N'-tetramethylethylenediamine are prepared for all of the probes. N,N,N',N'-tetramethylethylenediamine is added to the respective solutions, and immediately the respective solutions are dropwise added to the chip surface. The polymerization reaction is conducted in the atmosphere of helium. Of course, in the same manner as in the first embodiment, the reagents other than N,N,N',N'-tetramethylethylenediamine, that is, a solution wherein the Tris buffer containing acrylamide, N,N'-methylenebisacrylamide and ammonium persulfate are mixed with the polynucleotide probes having an acryl residue may be prepared, and then this solution may be dropwise added to the areas 87 on the surface of the polynucleotide probe chip.

Subsequently, the polynucleotide probe chip may be exposed to gasified or misted N,N,N',N'-tetramethylethylenediamine so as to start the polymerization reaction. Even if the reaction solution flows out from the areas 87, any gel is not produced on portions which Teflon is evaporated on. This is because Teflon usually absorbs and stores oxygen to block radical polymerization. The stored oxygen is not easily replaced. Gels 87 are produced in the electrodes 81 and 82 and the areas 87 having a double bond. After the gels 83 are produced, the hydrophilic portions 84 and 85 on which Teflon is evaporated are treated with 0.05% Tween 20 solution to cause hydrophilicity to be exhibited.

Figure 9:
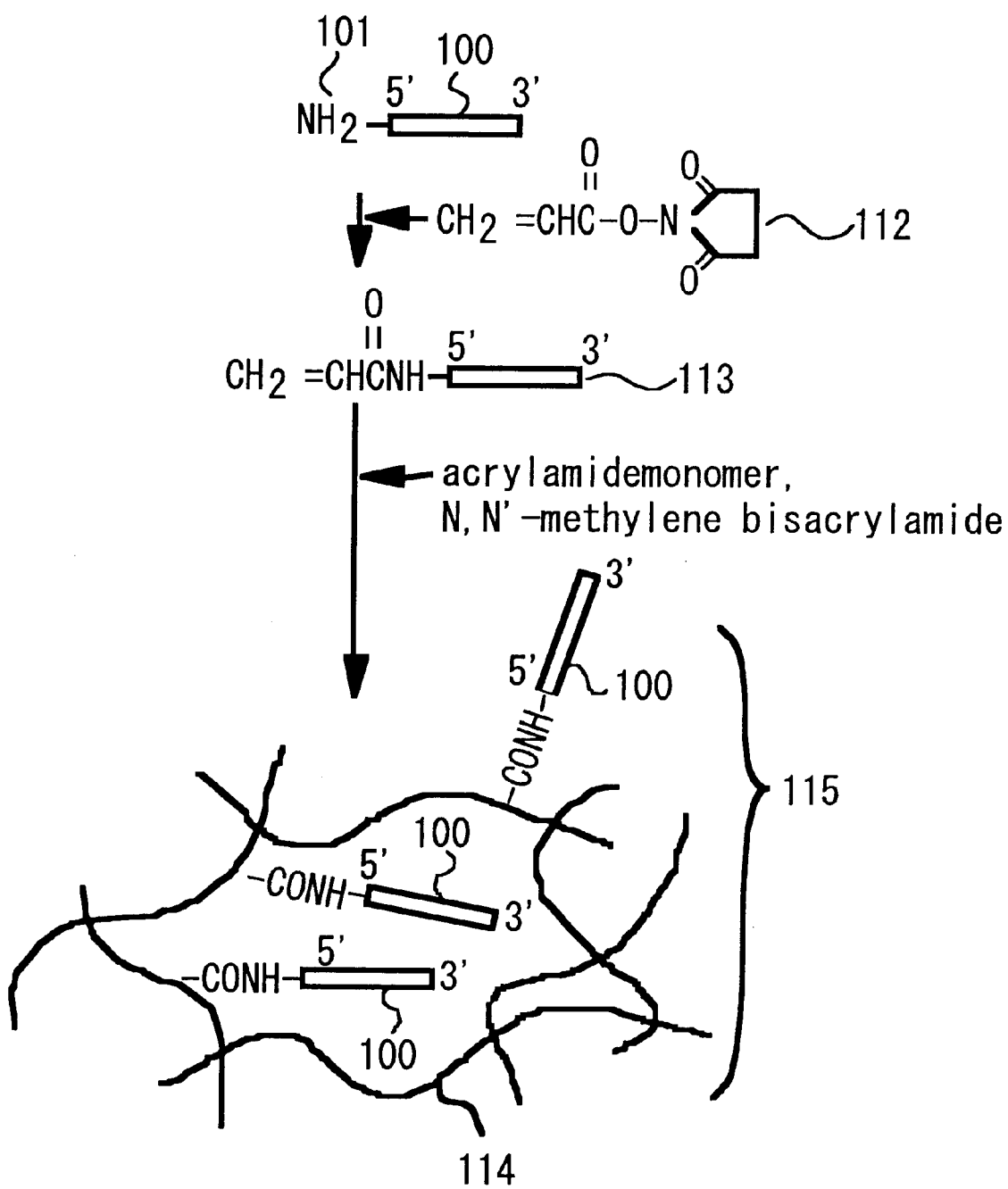
FIG. 9 is a view for explaining a method for obtaining polyacrylamide gels holding polynucleotide probes of the second embodiment according to the present invention.

FIG. 9 is a view for explaining a method for obtaining the polyacrylamide gel holding the polynucleotide probe having an acryl residue. Polynucleotide probes 100 having an amino acid residue 101 at the 5' terminal thereof are reacted with N-acryloxysuccinimide 112 at a pH of 9. The reactant is subjected to gel filtration to acryloxypolynucleotide probes 113. In the same manner as in the first embodiment, polyacrylamide gels 114 to which the polynucleotide probes 100 are fixed can be obtained as shown by reference number 115. The polyacrylamide gels 114 to which the polynucleotide probes 100 are fixed are the gels 83 holding the polynucleotide probes of the polynucleotide probe chip 79 shown in FIGS. 8A and 8B.

The following will describe an example wherein the thus produced polynucleotide probe chip 79 is used to assay DNA fragments actually. A sample is the same as in the first embodiment. That is, a human DNA clone (8.7 kb) is cut with a restriction enzyme Hsp92II and then labelled with a fluorophore to obtain a fragment group (The preparation thereof is according to that of the first embodiment). This fragment group is used as the sample. The following will describe an example wherein the probes of sequence Nos. 1 and 2 are used to detect DNA fragments complementary to these probes.

When 100 μL of the sample solution are dropwise added to the chip, the sample solution is surrounded, as shown by reference number 88 in FIG. 8B, by the hydrophobic portions 86 and 86', the hydrophilic electrodes 81 and 82 which are covered with the gels, and the hydrophilic portions 84 and 85, to be collected. It is sufficient that the sample solution contacts the gels 83 holding the polynucleotide probes. The amount of the sample solution may be large in such a manner that the gels 83 are completely immersed in the sample solution. An electrical potential of 0.5 V is applied between the electrode 82 (FIGS. 8A and 8B), as an anode, and the electrode 81, as a cathode. Thus, the DNA fragments in the sample solution are migrated in the gels by electrophoresis to perform hybridization. In the same way as in the first embodiment, the polarities of the electrodes are changed plural times at intervals of 5 seconds, so that the DNA fragments labelled with the fluorophore in the sample solution 88 are repeatedly migrated in the gels 83. The polarities of the electrodes are changed with a switch for changing the polarities, which is not shown in FIG. 8A or 8B. In the present example, the change is repeated 10 times at intervals of 5 seconds.

Thereafter, the whole of the cell is washed and then an electrical potential of 0.5 V is applied between the electrode 82, as an anode, and the electrode 81, as a cathode. Thus, unreacted DNA fragments in the gels are eluted out from the gels by electrophoresis. Furthermore, the cell is washed to remove non-hybridized DNA fragments, which cause a background. He–Ne laser light having a wavelength of 594 nm is radiated to the polynucleotide probe chip in which the reaction has finished. The emitted fluorescence is measured with a high sensitive cooled CCD from the upper face of the polynucleotide probe chip through a vapor deposited filter through which light having a wavelength of 605 to 660 nm transmits. In the above-mentioned manner, the target DNA fragment can be detected in the same way as in the first embodiment.

Third Embodiment

Figure 10:
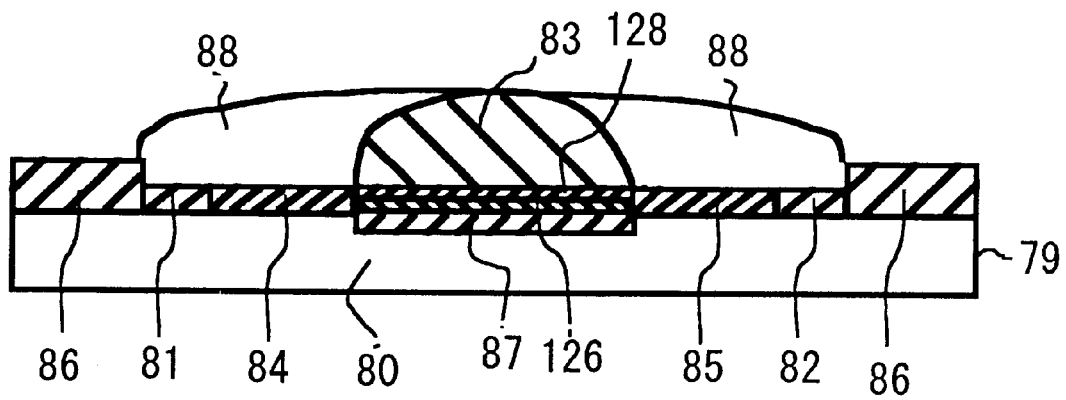
FIG. 10 is a cross section illustrating the structure of the polynucleotide probe chip of a third embodiment according to the present invention.

FIG. 10 is a cross section (corresponding to the section taken along the A–A' line in FIG. 8A) of the structure of the polynucleotide probe chip of the third embodiment. The structure shown in FIG. 10 is as follows. In the polynucleotide probe chip illustrated in FIGS. 8A and 8B related to the second embodiment, photodiodes 126 are formed in the respective areas 87 in which gels are produced, and further metallic vaporized layers 128 through which light having a specific wavelength (fluorescence emitted from a fluorescence label) transmits are formed on the photodiodes 126 through insulating layers (not shown). Polynucleotide probes (DNA probes)are fixed onto the surfaces of the metallic vaporized layers 128. The metallic vaporized layers 128 act as band pass filters for causing the luminous wavelength of the used fluorophore to pass.

In the same way as in the second embodiment, an electrical potential of 0.5 V is applied between the electrode 82 (in FIG. 10), as an anode, and the electrode 81, as a cathode. Thus, DNA fragments in the sample solution 88 are migrated in the gels 83 by electrophoresis to perform hybridization. The fragments labelled with the fluorophore are captured in the respective areas, and the whole of the cell is washed and then an electrical potential of 0.5 V is applied between the electrode 82, as an anode, and the electrode 81, as a cathode. Thus, unreacted DNA fragments in the gels 83 are eluted out from the gels 83 by electrophoresis. Next, the cell is washed to remove non-hybridized DNA fragments. The polarities of the electrodes are changed with a switch for changing the polarities, which is not shown in FIG. 10. Using the same structure as shown in FIG. 6, the polynucleotide probe chip in which the reaction has finished is irradiated with He—Ne laser light having a wavelength of 594 nm.

The emitted fluorescence is measured with the photodiodes 126 in the respective areas, and respective currents flowing in the respective photodiode are taken out through wiring formed on the surface of the polynucleotide probe chip. The fluorescence emitted from the sulforhodamine 101 is detected with the respective photodiodes 126 through the metallic vaporized layers 128 through which light having a wavelength of 605 to 660 nm transmits. In the above-mentioned manner, the target DNA fragment can be detected in the same way as in the first and second embodiments.

Fourth Embodiment

Figure 11:
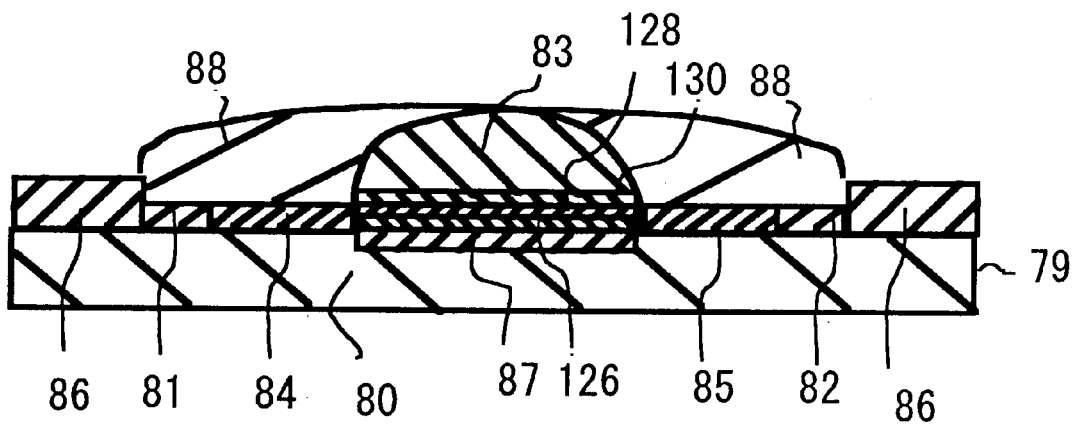
FIG. 11 is a cross section illustrating the structure of the polynucleotide probe chip of a fourth embodiment according to the present invention.

FIG. 11 is a cross section (corresponding to the section along the A–A' line in FIG. 8A) of the structure of the polynucleotide probe chip of the fourth embodiment. The structure shown in FIG. 11 is as follows. In the structure of the polynucleotide probe chip as the third embodiment, transparent electrodes 130 are formed on the metallic vaporized layers 128 through insulating layers (not shown). The transparent electrodes 130 have a structure which causes fluorescence emitted from an fluorophore to pass through the electrodes 130. The polynucleotide probes (DNA proves) are fixed onto the transparent electrodes 130.

An electrical potential of 0.5 V is applied between the transparent electrode 130, as cathodes, and the electrode 81 and 82 (FIG. 11), as anodes. Thus, DNA fragments in the sample solution 88 are migrated in the gels 83 by electrophoresis to perform hybridization. The fragments labelled with the fluorophore are captured in the respective areas. Thereafter, the whole of the cell is washed and then an electrical potential of 0.5 V is applied between the transparent electrodes 130, as anodes, and the electrodes 81 and 82 (in FIG. 11), as cathodes. Thus, unreacted DNA fragments in the gels 83 are eluted out from the gels 83 by electrophoresis. Next, the cell is washed to remove non-hybridized DNA fragments. The polarities of the transparent electrodes 130 and the electrodes (81 and 82) are changed with a switch for changing the polarities, which is not shown in FIG. 11.

Using the same structure as shown in FIG. 6, the polynucleotide probe chip in which the reaction has finished is irradiated with He—Ne laser light having a wavelength of 594 nm. In the same way as in the third embodiment, the emitted fluorescence is measured in each of the areas. However, the fluorescence is detected with the respective photodiodes 126 through the metallic vaporized layers 128 and the transparent electrodes 130. In the above-mentioned manner, the target DNA fragment can be detected in the same way as in the first, second and third embodiments.

Fifth Embodiment

Figure 12A:
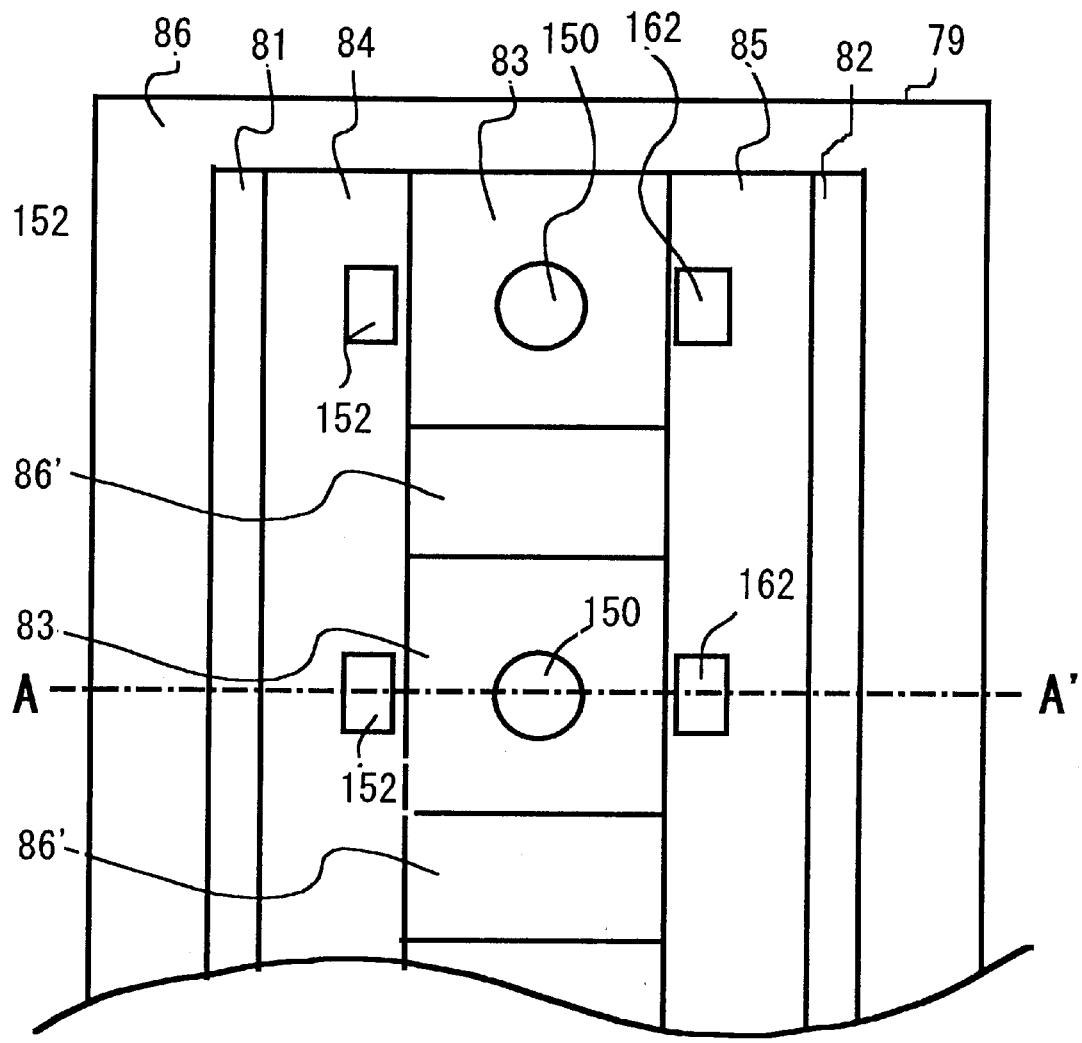
FIG. 12A is a plane view illustrating the structure of the polynucleotide probe chip of a fifth embodiment according to the present invention.
Figure 12B:
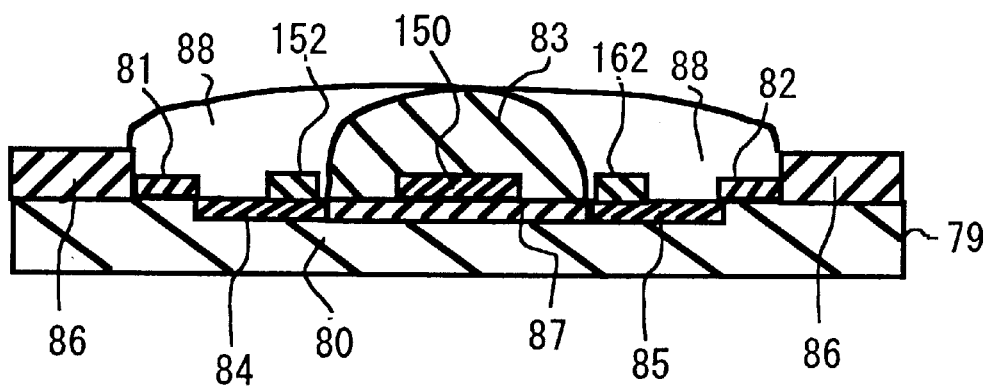
FIG. 12B is a cross section illustrating the structure of the polynucleotide probe chip of the fifth embodiment according to the present invention.

FIG. 12A is a plane view of a polynucleotide probe chip 79 of the fifth embodiment, and FIG. 12B is a cross section taken along the A–A' line in FIG. 12A. The structure shown in FIGS. 12A and 12B is as follows. In the structure of the polynucleotide probe chip illustrated in FIGS. 8A and 8B related to the second embodiment, the following are further arranged: point electrodes 150 (their area: 0.15 mm×0.15 mm) formed at the center of the respective areas 87 in which the polyacrylamide gels 83 are formed; and point electrodes 152 and 162 (their size: 0.1 mm along the A–A' direction, and 0.15 mm along the direction perpendicular to the A—A direction) which are formed outside the respective areas 87 and which the point electrodes 150 are arranged between. The center of the point electrode 150 is located 0.13 mm apart, in the A–A' direction, from the respective centers of the point electrodes 152 and 162. The polyacrylamide gel 83 is formed in the area 87, which is larger than the area of the point electrode 150.

In the structure shown in FIGS. 12A and 12B, a high frequency electrical potential is applied instead of a direct current, so that a sample DNA is introduced into polyacrylamide. In this way, the sample DNA and the polynucleotide probes which are fixed to the polyacrylamide matrix are effectively hybridized. The advantage based on the fact that the high frequency electrical potential is used is that no gas is generated by electrolysis and electrophoresis can be conducted for a long time. According to the application of a direct current in the fourth embodiment, there arises a problem that an electrical potential cannot be applied in a constant direction because of the generation of gas and the direction of the electrical potential must be changed at intervals of several seconds or such a low electrical potential that electrolysis is not caused must be applied. This problem can be overcome by using the high frequency field. However, a fully worked-out electrode arrangement is necessary for migrating the DNA molecules in a desired direction by application of the high frequency electrical potential.

The mixture solution of the sample DNA is dropwise added onto the surface of the polynucleotide probe chip, to immerse the electrodes 81, 82, 152 and 162 and the polyacrylamide gels in the mixture solution of the sample DNA. When a high frequency electrical potential of 2 MHz and 50 V is first applied between the point electrode 150 and the linear electrode 81, and between the point electrode 150 and the linear electrode 82, the DNA molecules in the mixture solution is shifted toward the point having a high electric field density along the gradient direction of the line of electric force. That is, the DNA molecules are shifted from the electrodes 81 and 82 to the point electrodes 150 to pass through the polyacrylamide gels. As a result, target DNA is hybridized with the polynucleotide probe fixing onto the gel matrix. The speed of the migration of the DNA molecules depends on the gradient of line of electric force and the size of the DNA. As the DNA molecules are larger, they are more easily shifted. Next, a high frequency electrical potential is applied between the point electrode 152 and the electrode 82, or between the point electrode 162 and the electrode 82 in order to remove the DNA molecules which are not hybridized with the polynucleotide probes.

Since the length of the electrodes 81 and 82 is longer than that of the electrodes 152 and 162, the density of the electric field is higher near the electrodes 152 and 162 than near the electrodes 81 and 82. Thus, the DNA molecules which are not hybridized and held in the gel matrix are migrated toward the electrodes 152 and 162, and are eluted out from the polyacrylamide gels.

In the fifth embodiment, there are prepared areas 87 to which polynucleotide probes, having a 50-base length, complementary to DNA originating from M13 phage are fixed. As samples, M13 phase and λ DNA are used. (1) M13 phase is cut with PstI and then dUTP labelled with a fluorescent dye Cy-5 at the 3' terminal is taken in by extension reaction using terminal deoxynucleotidyl transferase, to prepare M13 labelled with the fluorophore. (2) In the same way as in the item (1), λ DNA is cut with PstI and then dUTP labelled with a fluorescent dye Cy-5 at the 3' terminal is taken in by extension reaction using terminal deoxynucleotidyl transferase, to prepare λ DNA labelled with the fluorophore. The mixture of the products prepared in the items (1) and (2) is used as a sample mixture solution.

The sample mixture solution is dropwise added onto the surface of the polynucleotide probe chip, and then an electrical potential of 2 Hz is applied between the point electrodes 150 and the linear electrodes 81, and between the point electrodes 150 and the linear electrodes 82 for 2 minutes, to introduce the sample DNA into the polyacrylamide gels. Thereafter, in the same way, an electrical potential of 2 MHz is applied between the electrodes 162 and the electrodes 81 for 2 minutes. After the surface of the polynucleotide probe chip is washed, in the same way an electrical potential of 2 MHz is applied between the electrode 82 and the electrodes 152 for 2 minutes. Thereafter, the surface of the polynucleotide probe chip is washed.

The concave portion of the polynucleotide probe chip is filled with a cleaning liquid, and in this state a cover glass is put on the surface of the cleaning liquid. As shown in FIG. 6, laser light is radiated onto the side face of the polynucleotide probe chip, to detect the fluorescence generated from the polyacrylamide gels 83 in the respective areas 87. As a result, it is observed that the fluorescence intensity of the fluorescence emitted from the areas to which polynucleotide probes, having a 50-base length, complementary to DNA originating from M13 phage are fixed is 100–300 times larger than the fluorescence intensity of the fluorescence emitted from the areas to which the polynucleotide probes having other base sequence are fixed.

If the polynucleotide probe chip wherein the electrodes shown in FIGS. 12A and 12B are arranged is used, the application of a high frequency electrical potential makes it possible to handle the DNA molecules easily, for example, trap the DNA molecules in the polyacrylamide gels, or elute out the DNA molecules which are not hybridized with the polynucleotide probes from the polyacrylamide gels. Since no gas is generated by electrolysis, an electrical potential can be applied for a long time in the case that the polyacrylamide gels are directly formed on the surfaces of the electrodes. For this reason, the present embodiment is effective for concentrating specific DNA molecules from a dilute solution thereof by hybridization.

In the structure of the fifth embodiment, the following is allowable. In the same way as in the third embodiment, photodiodes having substantially the same area as the respective areas 87 are formed in the areas 87. Metallic vaporized layers 128 through which light having a specific wavelength range can transmit (fluorescence emitted from the fluorescence label) are formed on the photodiodes through insulating layers. Furthermore, in the same way as in the fourth embodiment, transparent electrodes 130 are formed on the metallic vaporized layers 128 through the insulating layers. These transparent electrodes 130 are used as the electrodes 150 shown in FIGS. 12A and 12B.

Sixth Embodiment

In the polynucleotide probe chip of the present invention, a great amount of the polynucleotide probes can be fixed onto the gel matrix. Therefore, the amount of DNA which can be captured by hybridization comes up to sub-pmol per area. Thus, more detailed analysis can be performed by collecting DNA captured in the respective areas. The following will describe a method for analyzing the captured DNA directly by using a capillary array electrophoresis device having plural capillaries, as the sixth embodiment.

Figure 13:
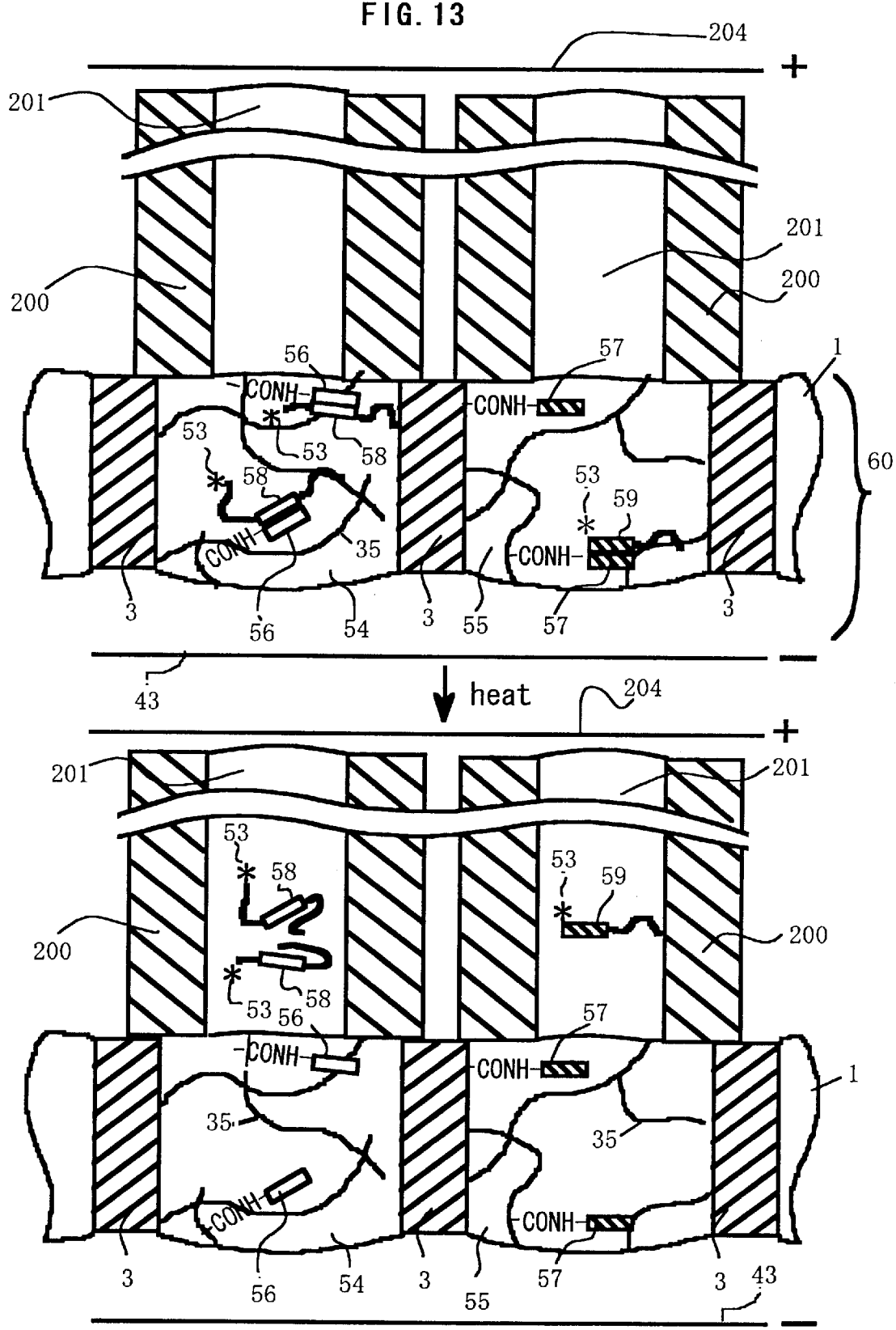
FIG. 13 is a cross section for explaining the structure and the action of a sixth embodiment according to the present invention, that is, a combination of a capillary array electrophoresis device and the polynucleotide probe chip of the first embodiment.

FIG. 13 is a cross section for explaining the structure and the action of the sixth embodiment wherein a capillary array electrophoresis device is combined with the polynucleotide probe chip of the first embodiment. In the sixth embodiment, as a sample, there is used a fragment group obtained by cutting a human DNA clone (8.7 kb) with a restriction enzyme HSP92II, in the same manner as in the first embodiment. The polynucleotide probe chip 1 (FIG. 5) on which the polynucleotide probes of sequence Nos. 1 and 2 are fixed is used to capture fragments complementary to the polynucleotide probe chip of sequence Nos. 1 and 2 in respective areas. The reference number 60 in the upper part of FIG. 13, which is the same as reference number 60 in the lower part of FIG. 5, represents the state that the fragments are captured in the respective areas.

As shown in FIG. 13, in the structure of the device of the sixth embodiment, the end of capillaries 200 is caused to adhere closely to each of areas 54 and 55 of the polynucleotide probe chip 1. The ends of the capillaries 200 are bundled in the form of a 16×16 matrix, in such a manner that the ends are fitted to the pattern of the arrangement of the areas of the chip 1. One of the capillaries 200 corresponds to and contacts each of the areas. That is, the centers of the ends of the capillaries 200 are two-dimensionally arranged at intervals of 1 mm. A crosslinked polyacrylamide gel 201 of T=4.5% and C=2.5% is formed as an electrophoresis separation carrier inside each of the capillaries.

The polyacrylamide gel inside each of the capillaries and at the one end thereof electrically contacts the gel formed in each of the areas of the polynucleotide probe chip, so that an electrical potential can be applied between an electrode 204 contacting the polyacrylamide gel inside each of the capillaries and at the other end thereof and an electrode 43.

When an infrared lamp is used to irradiate the polynucleotide probe chip with infrared light, the temperature of the chip rises so that DNA fragments having sequences 58 and 59, which are hybridized with the polynucleotide probes 56 and 57 fixed onto a gel matrix 35, are released.

The electrode 204 and the electrode 43 are used as an anode and as a cathode, respectively, to apply an electrical potential of 100 V/cm to the gel inside the each of the capillaries and each of the areas of the polynucleotide probe chip. The released DNA fragments in the respective areas are migrated to the respective capillaries by electrophoresis. The respective fragments have different electrophoresis speeds in accordance with their sizes; therefore, when the electrical potential is continuously applied for 30 minutes, the size of the DNA fragments captured in the respective areas can be known by the following: the respective capillaries are irradiated with laser light, at the side near the electrode 204, or alternatively there is used a laser radiating system and a fluorescence detecting system (not shown in FIG. 13) for radiating laser light from buffer solution outside the respective capillaries to excite the fluorescence label of the respective fragments, and detecting the emitted fluorescence. Of course, each size of the DNA fragments captured in the areas can be separated and collected, in synchronization with the above-mentioned detection of the fluorescence.

Seventh Embodiment

The following will describe the structure and the action of a device for collecting DNA fragments of the seventh embodiment wherein a capillary array electrophoresis device is combined with the second embodiment (FIGS. 8A and 8B), the third embodiment (FIG. 10), the fourth embodiment (FIG. 11), or the fifth embodiment (FIGS. 12A and 12B).

Figure 14:
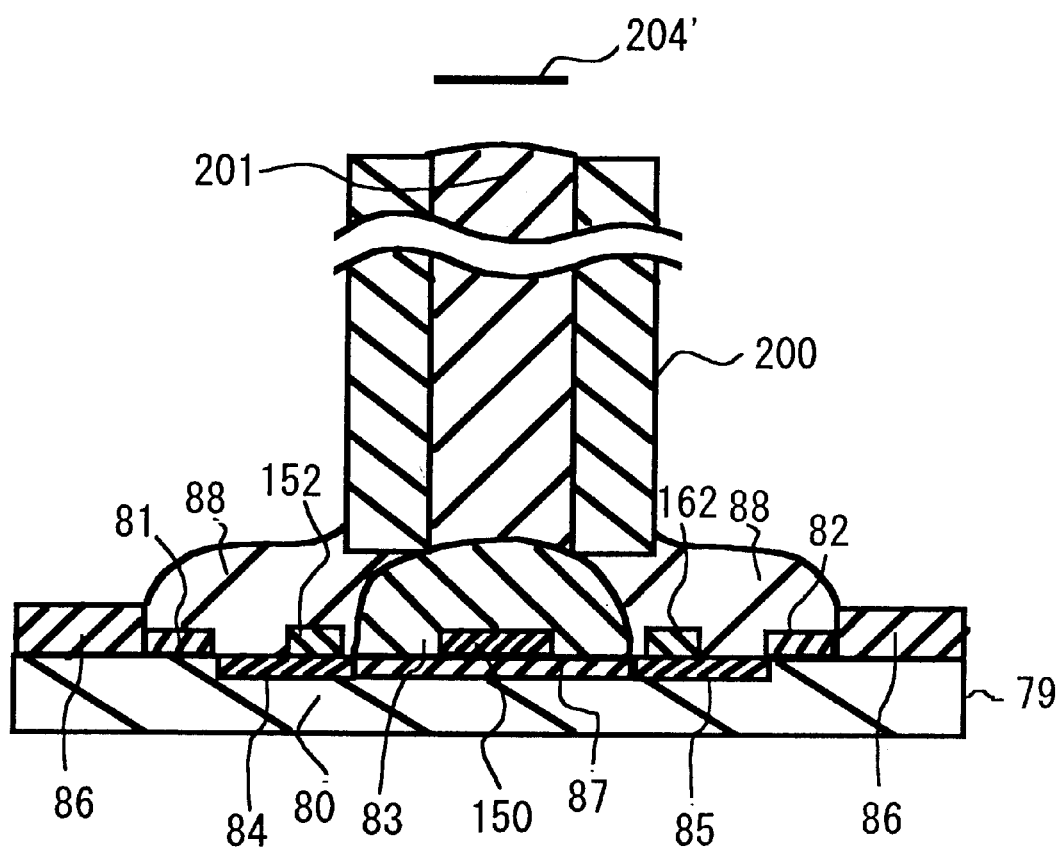
FIG. 14 is a cross section for explaining the structure and the action of a seventh embodiment according to the present invention, that is, a DNA fragment-collecting device wherein a capillary array electrophoresis device is combined with the fifth embodiment.

FIG. 14 is a cross section for explaining the structure and the action of a device for collecting DNA fragments of the seventh embodiment wherein a capillary array electrophoresis device is combined with the fifth embodiment (FIGS. 12A and 12B). In a gel matrix 83 to which polynucleotide probes in respective areas 87 are fixed, DNA fragments complementary to the polynucleotide probes are captured. The centers of the ends of 16 capillaries 200 contact a solution 88 and the gel matrix 83, and are one-dimensionally arranged at intervals of 0.75 mm, in such a manner that the centers of the areas 87 are consistent with the centers of ends at one side of the capillaries.

In the same manner as in the sixth embodiment, an infrared lamp is used to irradiate the surface of the polynucleotide probe chip 97 with infrared light. Thus, the chip is heated so that hybridized DNA fragments are released from the polynucleotide probes. Electrodes 152, 162 and 150 are then used as anodes and an electrode 204' contacting a polyacrylamide gel inside each of the capillaries at the opposite end is used as a cathode, to apply an electrical potential intensity of 50 V/cm for 30 seconds. Thus, the DNA fragments released from the gel matrix 83 are introduced to the capillaries 200. Since the volume of the sample solution 88 is a little, pH of the solution changes if the application of the electrical potential is continued. As a result, the electrophoresis is influenced. For this reason, the ends of the capillaries 200 are separated from the polynucleotide probe chip and migrated to an electrode vessel containing a sufficient amount of an electrolyte solution. Further electrophoresis is continued at an intensity of 200 V/cm. In the same manner as in the sixth embodiment, a laser radiating system and a fluorescence detecting system are arranged at the side of the other ends of the capillaries. From the time of the electrophoresis, the size of the DNA fragments captured in the polynucleotide probe chip can be measured.

FIG. 15 shows an example of the electrophoresis pattern of the DNA fragments obtained by collecting the DNA fragments hybridized with 16 areas of the polynucleotide probe chip 79 and measuring the fragments. It can be understood that, in the same manner as in the sixth embodiment, each size of the DNA fragments hybridized with different polynucleotide in the respective areas can be separated and collected.

The above explanation is concerned with the structure and the action of a device for collecting DNA fragments wherein a capillary array electrophoresis device is combined with the polynucleotide probe chip 79 as the fifth embodiment (FIGS. 12A and 12B). Of course, the capillary array electrophoresis device may be combined with the polynucleotide probe chip 79 as the second embodiment (FIGS. 8A and 8B), the third embodiment (FIG. 10), or the fourth embodiment (FIG. 11), instead of the fifth embodiment (FIGS. 12A and 12B). In the case of using the polynucleotide probe chip as the second embodiment (FIGS. 8A and 8B) or the third embodiment (FIG. 10), the electrodes 81 and 82 are used as cathodes. In the case of using the polynucleotide probe chip as the fourth embodiment (FIG. 11), the transparent electrode 130, and the electrodes 81 and 82 are used as cathodes.

In the above-mentioned respective embodiments, a sufficient amount of DNA fragments can be captured in the polynucleotide probe chip. Therefore, the captured DNA fragments can be analyzed in more detailed. In the case of using DNA captured on a sold phase, it is general for obtaining a sufficient amount of DNA to use a carrier having a very wide surface area, such as magnetic beads or porous beads. Conventionally, it is difficult to use the polynucleotide probe chip in the form of substantially flat plane so as to separate and collect DNA fragments.

In conventional separation using beads, DNA captured on a solid phase in any manner is generally eluted once to a solution and used. In many cases, however, the DNA is diluted at the time of the elution. Thus, concentration is usually necessary. In the respective embodiments of the present invention, different probes are fixed in an array form onto different areas, to make it possible to realize a device capable of separating and collecting various kinds of DNAs at a time.

The respective embodiments of the present invention also has an advantage that DNA fragments separated and collected from respective areas can be separated and assayed, without being again eluted in the solution, by using capillary electrophoresis directly, or the fragments after the separation can be collected as they are in a very small amount.

Based on the above-mentioned embodiments, the outline of the present invention will be described. In the present invention, the existence of polynucleotide(s) hybridized with specific polynucleotide(s) are detected in a light detector by fluorescence emitted by exciting fluorescence label with laser light. The fluorescence label is beforehand bonded to sample polynucleotide(s), or is added (bonded) to polynucleotide(s) hybridized with specific polynucleotide(s).

(1) A polynucleotide probe chip of the present invention, comprises plural areas holding different polynucleotide probes, gels which are held in the respective areas and hold the polynucleotide probes, and a means for migrating sample polynucleotide(s) in the gels of the respective areas by electrophoresis, thereby hybridizing the polynucleotide probe(s) held by the gel(s) and the sample polynucleotide(s). The respective polynucleotide probes have a common portion having a substantially common sequence composed of from a 10-base sequence to a 60-base sequence, and a recognizing portion of any 2-base sequence or any 3-base sequence combined with the 3' terminal of the common portion. Each of the kinds of the probes is held in each of the different areas.

(2) A method for producing a polynucleotide prove chip, of the present invention, comprises plural areas holding different polynucleotide probes, comprising the steps of:

preparing, beforehand, a monomer having a reaction residue and a polynucleotide probe set comprising plural kinds of polynucleotide probes having a residue bonded to the reaction residue; and mixing every kind of any polynucleotide probes selected from the polynucleotide probe set with the monomer and adding the mixture to each of the different areas, to gelatinize the mixture.

(3) A method for producing a polynucleotide probe chip, of the present invention, comprises plural areas holding different polynucleotide probes, comprising the steps of:

preparing, beforehand, a monomer having a reaction residue and a polynucleotide probe set comprising plural kinds of polynucleotide probes having a residue bonded to the reaction residue, mixing the monomer with each of polynucleotide probe groups comprising any plural probes selected from the polynucleotide probe set, and adding the mixture to each of the different areas to gelatinize the mixture.

(4) A method for detecting polynucleotide(s), of the present invention, comprises the steps of:

labeling sample polynucleotide(s) with a fluorophore, adding the fluorophore-labelled sample polynucleotide(s) to a polynucleotide probe chip comprising plural areas having gels holding different polynucleotide probes and migrating the fluorophore-labelled sample polynucleotide(s) in the gels of the respective areas by electrophoresis, to hybridize the polynucleotide probe (s) held in the gel(s) with the fluorophore-labelled sample polynucleotide(s) and capture the resultant hybrid(s), and detecting the sample polynucleotide(s) captured in the respective areas.

(5) Another method for detecting polynucleotide(s), of the present invention, comprises the steps of:

adding the fluorophore-labelled sample polynucleotide(s) to a polynucleotide probe chip comprising plural areas having gels holding different polynucleotide probes and migrating the fluorophore-labelled sample polynucleotide(s) in the gels of the respective areas by electrophoresis, to hybridize the polynucleotide probe (s) held in the gels with the fluorophore-labelled sample polynucleotide(s) and capture the resultant hybrid(s), labeling the polynucleotide probe(s) hybridized with the specific polynucleotide(s) with a fluorophore, and detecting the fluorophore-labelled polynucleotide probe (s) captured in the respective areas.

(6) A polynucleotide probe chip of the present invention comprises plural areas having gels holding different polynucleotide probes; and first and second electrodes for migrating sample polynucleotide(s) in the gels, between which the areas are arranged.

(7) Other method for detecting polynucleotide(s), of the present invention, comprises the steps of:

adding sample polynucleotide(s) to a polynucleotide probe chip comprising plural areas having gels holding different polynucleotide probes, on its substrate, changing, plural times, polarities of first and second electrodes for migrating sample polynucleotide(s) in the gels, between which the areas are arranged, to migrate the sample polynucleotide in the gels of the respective areas, thereby hybridizing the polynucleotide probe(s) held in the gel(s) with the sample polynucleotide(s).

(8) Other polynucleotide probe chip of the present invention comprises areas having gels holding different polynucleotide probes, and first and second electrodes between which the respective areas are arranged, the electrodes being for migrating sample polynucleotide(s) in the gels, thereby changing, plural times, polarities of the first and second electrodes to migrate sample polynucleotide(s) in the gels, to hybridize the polynucleotide probe(s) held in the gel(s) with the sample polynucleotide(s).

(9) A polynucleotide detecting device of the present invention comprises a polynucleotide probe chip comprising plural areas having gels holding different polynucleotide probes, on its substrate; a means for irradiating the gels of the areas with laser light, along the direction parallel to a main surface of the substrate; and a light detector for detecting emitted fluorescence along the direction perpendicular to the main surface of the substrate.

(10) Other method for detecting polynucleotide(s), of the present invention, comprises the step of using a polynucleotide probe chip comprising plural areas having gels holding different polynucleotide probes, and irradiating the gels of the areas simultaneously with laser light, along the direction parallel to a main surface of the substrate, thereby detecting emitted fluorescence along the direction perpendicular to the main surface of the substrate.

(11) Other polynucleotide probe chip of the present invention comprises plural areas having gels holding different polynucleotide probes, on its substrate; and light detecting elements arranged in the respective areas.

(12) Other method for detecting polynucleotide(s), of the present invention, comprises the steps of using a polynucleotide probe chip comprising plural areas having gels holding different polynucleotide probes, and irradiating the gels of the areas with laser light, along the direction parallel to a main surface of the substrate, thereby detecting fluorescence emitted by respective light detecting elements arranged in the respective areas, along the direction perpendicular to the main surface of the substrate.

(13) Other polynucleotide detecting device of the present invention comprises:

a polynucleotide probe chip comprising plural areas having gels holding different polynucleotide probes, on its substrate, and respective light detecting elements arranged in the respective areas; and a means for irradiating the gels of the areas with laser light, along the direction parallel to a main surface of the substrate.

(14) Other polynucleotide probe chip of the present invention comprises an optically transparent substrate, wherein a concave portion is formed; gels held in holes which are formed in a flat base face of the concave portion, penetrate the substrate and have a tapered side face; different polynucleotide probes held in the gels; and a portion for irradiating a side face of the substrate with laser light; thereby migrating sample polynucleotide(s) in the gels of the respective areas by electrophoresis, to hybridize the polynucleotide probe(s) held in the gel(s) with the sample polynucleotide(s).

(15) Other polynucleotide probe chip of the present invention comprises a substrate wherein a concave portion is formed; plural portions which are arranged in one direction and hold gels in a flat base face of the concave portion; first and second electrodes between which the plural portions are arranged; different polynucleotide probes held in the gels; and a portion for irradiating a side face of the substrate with laser light; thereby migrating sample polynucleotide(s) in the gels of the respective areas by electrophoresis, to hybridize the polynucleotide probe(s) held in the gel(s) with the sample polynucleotide(s).

(16) Other polynucleotide probe chip of the present invention comprises plural areas having gels holding different polynucleotide, on its substrate; light detecting elements arranged in the respective areas; band pass filters formed over the light detecting elements; first electrodes over the band pass filters; and second electrodes, between which the respective areas are arranged; thereby changing, plural times, polarities of the first and second electrodes to migrate sample polynucleotide(s) in the gels of the respective areas, thereby hybridizing the polynucleotide probe(s) held in the gel(s) with specific polynucleotide(s) among the sample polynucleotide(s).

(17) Other polynucleotide detecting device of the present invention comprises:

a polynucleotide probe chip comprising plural areas having gels holding different polynucleotide, on its substrate; light detecting elements arranged in the respective areas; band pass filters formed over the light detecting elements; first electrodes over the band pass filters, between which insulating layers are arranged; and second electrodes, between which the respective areas are arranged;

a means for changing polarities of the first and second electrodes; and a means for irradiating the gels of the areas with laser light, along the direction parallel to a main surface of the substrate.

(18) Other polynucleotide probe chip of the present invention comprises areas which have gels holding different polynucleotide probes and are arranged in a first direction; first electrodes arranged in the respective areas; and second electrodes between which the areas are arranged in the first direction;

thereby applying a high frequency electrical potential between the first and second electrodes and migrating sample polynucleotide(s) in the gels of the respective areas to hybridize the polynucleotide probe(s) held in the gel(s) with the sample polynucleotide(s).

(19) Other polynucleotide probe chip of the present invention comprises areas which have gels holding different polynucleotide probes and are arranged in a first direction; first electrodes arranged in the respective areas; second electrodes between which the areas are arranged in the first direction; and third electrodes arranged between the first and second electrodes;

thereby applying a high frequency electrical potential between the first and second electrodes and migrating sample polynucleotide(s) in the gels of the respective areas to hybridize the polynucleotide probe(s) held in the gel(s) with the sample polynucleotide(s), and further applying a high frequency electrical potential between the second and third electrodes to migrate the sample polynucleotide(s) which are not hybridized with the polynucleotide(s) held in the gel(s) from the gels.

(20) Other polynucleotide detecting device of the present invention comprises:

a polynucleotide probe chip comprising plural areas holding different polynucleotide probes, and gels held in the respective areas and holding the polynucleotide probes;

a means for migrating sample polynucleotide(s) in the gels of the respective areas by electrophoresis, thereby hybridizing the polynucleotide probe(s) held in the gel(s) with the sample polynucleotide(s);

a means for releasing the sample polynucleotide(s) from the polynucleotide probe(s) with which the sample polynucleotide(s) are hybridized; and capillaries for separating the released sample polynucleotide(s) by electrophoresis, the capillaries being arranged correspondingly to the respective areas.

(21) Other method for detecting polynucleotide(s) of the present invention comprises the steps of:

adding sample polynucleotide(s) to a polynucleotide probe chip comprising areas which have gels holding different polynucleotide probes and are arranged in a first direction; first electrodes arranged in the respective areas, and second electrodes between which the areas are arranged in the first direction; and applying a high frequency electrical potential between the first and second electrodes, to migrate the sample polynucleotide(s) in the gels of the respective areas, thereby hybridizing the polynucleotide probe(s) held in the gel(s) with the sample polynucleotide(s).

(22) Other polynucleotide assaying method of the present invention comprises the steps of:

adding sample polynucleotide(s) to a polynucleotide probe chip comprising, on its substrate, areas which have gels holding different polynucleotide probes and are arranged in a first direction; first electrodes arranged in the respective areas; second electrodes between which the areas are arranged in the first direction; and third electrodes arranged between the first and second electrodes;

applying a high frequency electrical potential between the first and second electrodes and migrating sample polynucleotide(s) in the gels of the respective areas to hybridize the polynucleotide probe(s) held in the gel(s) with the sample polynucleotide(s), and applying a high frequency electrical potential between the second and third electrodes to migrate the sample polynucleotide(s) which are not hybridized with the polynucleotide(s) held in the gel(s) from the gels.

(23) Other polynucleotide assaying method of the present invention comprises the steps of:

adding sample polynucleotide(s) to a polynucleotide probe chip comprising areas having gels holding different probes, migrating the sample polynucleotide(s) in the gels of the respective areas by electrophoresis, to hybridize the polynucleotide probe(s) held in the gel(s) with the sample polynucleotide(s)

releasing the sample polynucleotide(s) from the polynucleotide probe(s) with which the sample polynucleotide(s) are hybridized; and using capillaries arranged correspondingly to the respective areas, to separate the released sample polynucleotide s) by electrophoresis.

What is claimed is:

1. A polynucleotide detecting device comprising:

a polynucleotide probe chip comprising a substrate having a concave portion; gels immobilized in holes which are formed in a flat surface of the concave portion, penetrate the substrate and have tapered side faces; and different polynucleotide probes immobilized in the gels;

an electrode vessel in which a first electrode is located, and in which a lower surface of the polynucleotide probe chip is located;

a second electrode which is set in a solution including sample polynucleotides added onto an upper surface of the polynucleotide probe chip; and a switch which changes, plural times, polarities of the first and second electrodes, to migrate the sample polynucleotides in the gels of the respective holes by electrophoresis, thereby hybridizing the polynucleotide probes immobilized in the gels with the sample polynucleotides.

2. A polynucleotide detecting device according to claim 1, wherein the polynucleotide probes each have, at the 5'-end, a common base sequence which is common to base sequences of all the polynucleotide probes and recognizing base sequence at the 3'-end of each of the polynucleotide probes for the sample polynucleotides, the common base sequence is composed of 10 bases to 60 bases, and the recognizing base sequence at the 3'-end of the common base sequence is composed of 2 bases or 3 bases, and each of the different polynucleotide probes is immobilized in each of the different areas.

3. A method for producing a polynucleotide probe chip comprising plural areas immobilizing different polynucleotide probes, the method comprising the steps of:

preparing a polynucleotide probe set comprising plural kinds of polynucleotide probes having an active acryl residue at the 5'-end; and mixing each of the polynucleotide probes selected from the polynucleotide probe set and an acrylamide monomer or derivative thereof and adding the mixture to each of the different areas fixing a reagent having an active acryl residue at a part of a chain aliphatic compound, to gelatinize the mixture in the respective areas.

4. A method for detecting polynucleotides comprising the steps of:

labeling sample polynucleotides with fluorophores;

adding the fluorophore-labeled sample polynucleotides to a polynucleotide probe chip comprising plural areas having gels immobilizing different polynucleotide probes, and comprising first and second electrodes for migrating the fluorophore-labeled sample polynucleotides in the gels, between which the plural areas are arranged;

changing, plural times, polarities of the first and second electrodes, and migrating the fluorophore-labeled sample polynucleotides in the gels of the respective areas by electrophoresis, to hybridize the polynucleotide probes immobilized in the gels with the fluorophore-labeled sample polynucleotides and to form hybrids; and detecting the fluorophore-labeled sample polynucleotides forming the hybrids in the respective areas.

5. A method for detecting polynucleotides comprising the steps of:

adding sample polynucleotides to a polynucleotide probe chip comprising plural areas having gels immobilizing different polynucleotide probes, and comprising first and second electrodes for migrating the sample polynucleotides in the gels, between which the plural area are arranged;

changing, plural times, polarities of the first and second electrodes, and migrating the sample polynucleotides in the gels of the respective areas by electrophoresis, to hybridize the polynucleotide probes immobilized in the gels with the sample polynucleotides and to form hybrids;

introducing, by using DNA polymerase, a fluorophore-labeled dNTP or a fluorophore-labeled ddNTP into extended chains of the polynucleotide probes forming the hybrids to form fluorophore-labeled polynucleotide probes; and detecting the fluorophore-labeled polynucleotide probes forming the hybrids in the respective areas.

6. A polynucleotide probe chip comprising:

plural areas having gels immobilizing different polynucleotide probes; and first and second electrodes for migrating sample polynucleotides in the gels, between which the plural areas are arranged, polarities of the first and second electrodes being changed, plural times, to migrate the sample polynucleotides in the gels of the respective areas by electrophoresis, thereby hybridizing the polynucleotide probes immobilized in the gels with the sample polynucleotides.

7. A method for detecting polynucleotides comprising the steps of:

adding sample polynucleotides to a polynucleotide probe chip comprising plural areas having gels immobilizing different polynucleotide probes, on surfaces of respective areas of a substrate of the polynucleotide probe chip, and comprising first and second electrodes for migrating the sample polynucleotides in the gels, between which the plural areas are arranged; and changing, plural times, polarities of the first and second electrodes, and migrating the sample polynucleotides in the gels of the respective areas by electrophoresis, thereby hybridizing the polynucleotide probes immobilized in the gels with the sample polynucleotides.

8. A polynucleotide probe chip comprising:

plural areas having gels immobilizing different polynucleotide probes; and first and second electrodes between which the plural areas are arranged, the electrodes being for migrating sample polynucleotides in the gels, thereby changing, polarities of the first and second electrodes to migrate the sample polynucleotides in the gels by electrophoresis, and to hybridize the polynucleotide probes immobilized in the gels with the sample polynucleotides.

9. A polynucleotide detecting device comprising:

a polynucleotide probe chip comprising an optically transparent substrate having a concave portion; gels immobilized in holes which are formed in a flat surface of the concave portion, penetrate the substrate and have tapered side faces; different polynucleotide probes immobilized in the gels; and a portion for irradiating a side surface of the substrate with laser light;

an electrode vessel in which a first electrode is located, and in which a lower surface of the polynucleotide probe chip is located;

a second electrode which is set in a solution including sample polynucleotides added onto an upper surface of the polynucleotide probe chip; and a switch which changes, plural times, polarities of the first and second electrodes, to migrate the sample polynucleotides in the gels of the respective holes by electrophoresis, thereby hybridizing the polynucleotide probes immobilized in the gels with the sample polynucleotides;

a means for irradiating the gels of the respective holes with laser light, along a direction parallel to a main surface of the substrate; and light detector for detecting emitted fluorescence emitted in the respective holes from a direction perpendicular to the main surface of the substrate.

10. A method for detecting polynucleotides using a polynucleotide probe chip comprising plural areas having gels immobilizing different polynucleotide probes, and comprising first and second electrodes for migrating sample polynucleotides in the gels, between which the plural areas are arranged, the method comprising the steps of:

changing, plural times, polarities of the first and second electrodes, and migrating the sample polynucleotides in the gels of the respective areas by electrophoresis, thereby hybridizing the polynucleotide probes immobilized in the gels with the sample polynucleotides;

irradiating the gels of the areas simultaneously with laser light, along a direction parallel to a main surface of a substrate of the polynucleotide probe chip; and detecting emitted fluorescence along a direction perpendicular to the main surface of the substrate.

11. A polynucleotide probe chip comprising:

plural areas having gels immobilizing different polynucleotide probes, on surfaces of respective areas of a substrate of the polynucleotide probe chip;

first and second electrodes for migrating sample polynucleotides in the gels, between which the plural areas are arranged, polarities of the first and second electrodes being changed, plural times, to migrate the sample polynucleotides in the gels of the respective areas by electrophoresis, thereby hybridizing the polynucleotide probes immobilized in the gels with the sample polynucleotides;

photodiodes formed on surfaces of the respective areas.

12. A polynucleotide detecting device comprising:

a polynucleotide probe chip comprising plural areas having gels immobilizing different polynucleotide probes, on surfaces of respective areas of a substrate of the polynucleotide probe chip; photodiodes formed on surfaces of the respective areas; and first and second electrodes for migrating sample polynucleotides in the gels, between which the plural areas are arranged;

a switch which changes, plural times, polarities of the first and second electrodes, to migrate the sample polynucleotides in the gels of the respective areas by electrophoresis, thereby hybridizing the polynucleotide probes immobilized in the gels with the sample polynucleotides; and a means for irradiating the gels of the areas with laser light, along a direction parallel to a main surface of the substrate.

13. A polynucleotide probe chip comprising:

a substrate having a concave portion;

plural portions which are arranged in one direction and immobilize gels in a flat base face of the concave portion:

first and second electrodes between which the plural portions are arranged;

different polynucleotide probes immobilized in the gels;

a portion for irradiating a side surface of the substrate with laser light; and first and second electrodes for migrating sample polynucleotides in the gels, between which the plural portions are arranged, polarities of the first and second electrodes being changed, plural times, to migrate the sample polynucleotides in the gels of the respective potions by electrophoresis, thereby hybridizing the polynucleotide probes immobilized in the gels with the sample polynucleotides.

14. A polynucleotide probe chip comprising:

plural areas having gels immobilizing different polynucleotide probes, on surfaces of respective areas of a substrate of the polynucleotide probe chip;

photodiodes formed on surfaces of the respective areas;

band pass filters formed over the respective photodiodes;

first electrodes formed over the respective band pass filters; and second electrodes between which the plural areas are arranged, polarities of the first and second electrodes being changed, plural times, to migrate sample polynucleotides in the gels of the respective areas by electrophoresis, thereby hybridizing the polynucleotide probes immobilized in the gel(s) with the sample polynucleotides.

15. A polynucleotide detecting device comprising:

a polynucleotide probe chip comprising plural areas having gels immobilizing different polynucleotide probes on surfaces of respective areas of a substrate of the polynucleotide probe chip;

photodiodes formed on surfaces of the respective areas; first electrodes formed over the respective band pass filters, between which insulating layers are arranged; and means for changing, plural times, polarities of the first and second electrodes to migrate sample polynucleotides in the gels of the respective areas by electrophoresis, thereby hybridizing the polynucleotide probes immobilized in the gels with the sample polynucleotides; and a means for irradiating the gels of the areas with laser light, along a direction parallel to a main surface of the substrate.

16. A polynucleotide probe chip comprising:

plural areas having gels immobilizing different polynucleotide probes and being arranged in one direction;

first electrodes arranged in the respective areas; and second electrodes between which the plural areas are arranged in the one direction;

wherein a high frequency electrical potential is applied between the first and second electrodes and sample polynucleotides migrate in the gels of the respective areas by electrophoresis, to hybridize the polynucleotide probes immobilized in the gels with the sample polynucleotides.

17. A polynucleotide probe chip comprising:

plural areas having gels immobilizing different polynucleotide probes and being arranged in one direction;

first electrodes arranged in the respective areas;

second electrodes between which the plural areas are arranged in the one direction; and third electrodes arranged between the first and second electrodes;

wherein a high frequency electrical potential is applied between the first and second electrodes and sample polynucleotides migrate in the gels of the respective areas by electrophoresis, to hybridize the polynucleotide probes immobilized in the gels with the sample polynucleotides, and, in addition, a high frequency electrical potential is applied between the second and third electrodes to migrate, by electrophoresis, the sample polynucleotides which are not hybridized with the polynucleotide probes immobilized in the gels from the gels.

18. A polynucleotide detecting device comprising:

a polynucleotide probe chip comprising plural areas having gels immobilizing different polynucleotide probes, and comprising first and second electrodes for migrating sample polynucleotides in the gels, between which the plural area are arranged;

a means for changing, plural times, polarities of the first and second electrodes to migrate the sample polynucleotides in the gels of the respective areas by electrophoresis, thereby hybridizing the polynucleotide probes immobilized in the gels with the sample polynucleotides;

a means for releasing the sample polynucleotides from the polynucleotide probes with which the sample polynucleotides are hybridized; and capillaries for separating the released sample polynucleotides by electrophoresis, ends of the capillaries being arranged at intervals same as intervals of the respective areas.

19. A method detecting polynucleotides comprising the steps of:

adding sample polynucleotides to a polynucleotide probe chip comprising plural areas having gels immobilizing different polynucleotide probes and being arranged in one direction; first electrodes arranged in the respective areas; and second electrodes between which the plural areas are arranged in the one direction; and applying a high frequency electrical potential between the first and second electrodes and migrating the sample polynucleotides in the gels of the respective areas by electrophoresis, thereby hybridizing the polynucleotide probes immobilized in the gels with the sample polynucleotides.

20. A polynucleotides assay method comprising the steps of:

adding sample polynucleotides on a surface of a polynucleotide probe chip comprising plural areas having gels immobilizing different polynucleotide probes and being arranged in a one direction; first electrodes arranged in the respective areas; and second electrodes between which the plural areas are arranged in the one direction; and third electrodes arranged between the first and second electrodes;

applying a high frequency electrical potential between the first and second electrodes and migrating the sample polynucleotides in the gels of the respective areas by electrophoresis, to hybridize the polynucleotide probes immobilized in the gels with the sample polynucleotides; and applying a high frequency electrical potential between the second and third electrodes to migrate, by electrophoresis, the sample polynucleotides which are not hybridized with the polynucleotide probes immobilized in the gels from the gels.

21. A polynucleotide assay method comprising the steps of:

adding sample polynucleotides to a polynucleotide probe chip comprising plural areas having gels immobilizing different polynucleotide probes, and comprising first and second electrodes for migrating the sample polynucleotides in the gels, between which the plural areas are arranged;

changing, plural times, polarities of the first and second electrodes to migrate the sample polynucleotides in the gels of the respective areas by electrophoresis, thereby hybridizing the polynucleotide probes immobilized in the gels with the sample polynucleotides;

releasing the sample polynucleotides from the polynucleotide probes with which the sample polynucleotides are hybridized; and using capillaries arranged at intervals same as intervals of the respective areas, collecting and separating the released sample polynucleotides by electrophoresis.

22. A polynucleotide probe chip comprising:

plural areas having gels immobilizing different polynucleotide probes, the plural areas being arranged in one direction;

first and second electrodes for migrating sample polynucleotides in the gels, between which the plural areas are arranged, the first and second electrodes being arranged in the one direction; and photodiodes formed on surfaces of the respective areas.

23. A polynucleotide detecting device comprising:

a polynucleotide probe chip comprising plural areas having gels immobilizing different polynucleotide probes, the plural areas being arranged in one direction; photodiodes formed on surfaces of the respective areas; and first and second electrodes for migrating sample polynucleotides in the gels, between which the plural areas are arranged, the first and second electrodes being arranged in the one direction; and a means for irradiating the gels of the areas with laser light, along a direction parallel to a main surface of a substrate of the polynucleotide probe chip.

24. A polynucleotide probe chip comprising:

plural areas having gels immobilizing different polynucleotide probes, the plural areas being arranged in one direction;

first and second electrodes for migrating sample polynucleotides in the gels, between which the plural areas are arranged, the first and second electrodes being arranged in the one direction;

photodiodes formed on surfaces of the respective areas; and band pass filters formed on surfaces of the respective photodiodes through respective insulating layers.

25. A polynucleotide detecting device comprising:

a polynucleotide probe chip comprising plural areas having gels immobilizing different polynucleotide probes, the plural areas being arranged in one direction; first and second electrodes for migrating sample polynucleotides in the gels, between which the plural areas are arranged, the first and second electrodes being arranged in the one direction; photodiodes formed on surfaces of the respective areas; and band pass filters formed on surfaces of the respective photodiodes through respective insulating layers;

a means for irradiating the gels of the areas with laser light, along a direction parallel to a main surface of a substrate of the polynucleotide probe chip.

26. A polynucleotide probe chip comprising:

plural areas having gels immobilizing different polynucleotide probes, the plural areas being arranged in one direction;

first and second electrodes between which the plural areas are arranged, the first and second electrodes being arranged in the one direction;

photodiodes formed on surfaces of the respective areas;

band pass filters formed on surfaces of the respective photodiodes through respective insulating layers; and transparent electrodes formed on the band pass filters through respective insulating layers.

27. A polynucleotide detecting device comprising:

a polynucleotide probe chip comprising plural areas having gels immobilizing different polynucleotide probes, the plural areas being arranged in one direction; first and second electrodes between which the plural areas are arranged, the first and second electrodes being arranged in the one direction; photodiodes formed on surfaces of the respective areas; band pass filters formed on surfaces of the respective photodiodes through respective insulating layers; transparent electrodes formed on the band pass filters through respective insulating layers; and a means for irradiating the gels of the areas with laser light, along a direction parallel to a main surface of a substrate of the polynucleotide probe chip.

28. A polynucleotide probe chip comprising:

plural areas having gels immobilizing different polynucleotide probes, the plural areas being arranged in one direction;

first and second electrodes between which the plural areas are arranged, the first and second electrodes being arranged in the one direction;

first point electrodes formed on surfaces of the respective areas;

second point electrodes formed on a surface between the first point electrode and the first electrode; and third point electrodes formed on a surface between the first point electrode and the second electrode.

29. A polynucleotide detecting device comprising:

a polynucleotide probe chip comprising plural areas having gels immobilizing different polynucleotide probes, the plural areas being arranged in one direction; first and second electrodes between which the plural areas are arranged, the first and second electrodes being arranged in the one direction; first point electrodes formed on surfaces of the respective areas; second point electrodes formed on a surface between the first point electrode and the first electrode; third point electrodes formed on a surface between the first point electrode and the second electrode;

a means for irradiating the gels of the respective areas with laser light, along a direction parallel to a main surface of a substrate of the polynucleotide probe chip; and light detector for detecting emitted fluorescence emitted in the respective areas form a direction perpendicular to the main surface of a substrate of the polynucleotide probe chip.

* * * * *